(12) United States Patent
Galie et al.

(10) Patent No.: US 10,052,237 B2
(45) Date of Patent: *Aug. 21, 2018

(54) BONDING APPARATUS AND METHOD

(71) Applicant: The Procter & Gamble Company, Cincinnati, OH (US)

(72) Inventors: Theresa Lynn Galie, Cincinnati, OH (US); Joseph Allen Eckstein, Sunman, IN (US); Hailing Bao, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 331 days.

This patent is subject to a terminal disclaimer.

(21) Appl. No.: 14/301,416

(22) Filed: Jun. 11, 2014

(65) Prior Publication Data
US 2014/0377513 A1  Dec. 25, 2014

Related U.S. Application Data

(60) Provisional application No. 61/836,745, filed on Jun. 19, 2013.

(51) Int. Cl.
*A61F 13/15* (2006.01)
*B29C 65/60* (2006.01)
(Continued)

(52) U.S. Cl.
CPC .. *A61F 13/15585* (2013.01); *A61F 13/15577* (2013.01); *A61F 13/15699* (2013.01);
(Continued)

(58) Field of Classification Search
USPC .......... 156/60, 137, 219, 181, 182, 582; 428/194, 195.1, 196; 604/365, 387
See application file for complete search history.

(56) References Cited

U.S. PATENT DOCUMENTS 3,860,003 A   1/1975  Buell
3,961,119 A   6/1976  Thomas
(Continued)

FOREIGN PATENT DOCUMENTS

EP   1 635 750 B1   10/2009
JP   H08-511709    12/1996
(Continued)

OTHER PUBLICATIONS

PCT International Search Report, dated Sep. 17, 2014, 9 pages.
(Continued)

*Primary Examiner* — Lynda Salvatore
(74) *Attorney, Agent, or Firm* — Charles R. Matson

(57) ABSTRACT

The present disclosure relates to methods and apparatuses for mechanically bonding substrates together. The apparatuses may include a pattern roll having three or more pattern elements protruding radially outward, wherein each pattern element includes a pattern surface. The pattern surfaces are also separated from each other by gaps having minimum widths. The pattern roll may be adjacent an anvil roll to define a nip between the pattern surfaces and the anvil roll, wherein the pattern roll is biased toward the anvil roll to define a nip pressure between pattern surfaces and the anvil roll. As substrates advance between the pattern roll and anvil roll, the substrates are compressed between the anvil roll and the pattern surfaces to form a discrete bond region between the substrates. During the bonding process, some of yielded substrate material also flows from under the pattern surfaces and into the gaps to form gap grommet regions.

7 Claims, 19 Drawing Sheets

(51) Int. Cl.
| | |
|---|---|
| *B29C 65/78* | (2006.01) |
| *B29C 65/82* | (2006.01) |
| *B29C 65/00* | (2006.01) |
| *B29C 65/02* | (2006.01) |
| *B29C 65/56* | (2006.01) |
| B29L 31/48 | (2006.01) |
| B29C 65/52 | (2006.01) |
| B29C 65/18 | (2006.01) |

(52) U.S. Cl.
CPC .. *A61F 13/15731* (2013.01); *A61F 13/15739* (2013.01); *B29C 65/02* (2013.01); *B29C 65/56* (2013.01); *B29C 65/609* (2013.01); *B29C 65/7841* (2013.01); *B29C 65/7894* (2013.01); *B29C 65/8223* (2013.01); *B29C 66/02241* (2013.01); *B29C 66/1122* (2013.01); *B29C 66/21* (2013.01); *B29C 66/43* (2013.01); *B29C 66/431* (2013.01); *B29C 66/81429* (2013.01); *B29C 66/83411* (2013.01); *B29C 66/83415* (2013.01); *B29C 66/83511* (2013.01); *B29C 66/929* (2013.01); A61F 2013/15991 (2013.01); B29C 65/18 (2013.01); B29C 65/522 (2013.01); B29C 66/232 (2013.01); B29C 66/71 (2013.01); B29C 66/727 (2013.01); B29C 66/729 (2013.01); B29C 66/7294 (2013.01); B29C 66/72327 (2013.01); B29C 66/72343 (2013.01); B29L 2031/4878 (2013.01); Y10T 428/2481 (2015.01)

(56) References Cited

U.S. PATENT DOCUMENTS

| | | | |
|---|---|---|---|
| 4,264,659 A | 4/1981 | Pattenden | |
| 4,333,979 A | 6/1982 | Sciarafth et al. | |
| 4,610,678 A | 9/1986 | Weisman et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 3/1989 | Dragoo | |
| 4,823,783 A | 4/1989 | Willhite, Jr. et al. | |
| 4,834,735 A | 5/1989 | Alemany et al. | |
| 4,854,984 A | 8/1989 | Ball et al. | |
| 4,888,231 A | 12/1989 | Angstadt | |
| 4,909,803 A | 3/1990 | Aziz et al. | |
| 5,036,758 A | 8/1991 | Kobayashi | |
| 5,057,357 A | 10/1991 | Winebarger | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,798,167 A | 8/1998 | Connor | |
| 5,817,199 A | 10/1998 | Brennecke et al. | |
| 5,861,081 A | 1/1999 | Bredendick et al. | |
| 5,871,605 A | 2/1999 | Bett | |
| 5,916,661 A | 6/1999 | Benson et al. | |
| 5,954,625 A | 9/1999 | Giesler, Sr. | |
| 6,080,276 A | 6/2000 | Burgess | |
| 6,093,665 A | 7/2000 | Sayovitz | |
| 6,106,929 A | 8/2000 | Bredenick et al. | |
| 6,107,539 A | 8/2000 | Palumbo et al. | |
| 6,173,496 B1 | 1/2001 | Makoui | |
| 6,193,918 B1 | 2/2001 | McGuire | |
| 6,302,998 B1 | 10/2001 | Burgess | |
| 6,395,133 B1 | 5/2002 | McNeil | |
| 6,440,564 B1 | 8/2002 | McLain | |
| 6,537,644 B1 | 3/2003 | Kauschke | |
| 6,545,197 B1 | 4/2003 | Muller et al. | |
| 6,602,454 B2 | 8/2003 | McGuire | |
| 6,610,390 B1 | 8/2003 | Kauschke | |
| 6,713,159 B1 * | 3/2004 | Blenke | A61F 13/496 428/195.1 |
| 6,733,605 B1 | 5/2004 | Lamping | |
| 6,746,437 B2 | 6/2004 | Blenke | |
| 6,766,937 B2 | 7/2004 | Stegelmann | |
| 6,767,420 B2 | 7/2004 | Stegelmann | |
| 6,773,647 B2 | 8/2004 | McGuire | |
| 6,786,383 B2 | 9/2004 | Stegelmann | |
| 6,790,798 B1 | 9/2004 | Suzuki et al. | |
| 6,832,547 B2 | 12/2004 | Makoui | |
| 6,841,921 B2 | 1/2005 | Stegelmann | |
| 6,869,006 B2 | 3/2005 | Franklin | |
| 6,872,274 B2 | 3/2005 | Kauschke | |
| 6,942,755 B2 | 9/2005 | Basler | |
| 6,945,185 B2 | 9/2005 | Ribble | |
| 6,957,608 B1 | 10/2005 | Hubert | |
| 7,056,404 B2 | 6/2006 | McFall | |
| 7,178,316 B2 | 2/2007 | Kume et al. | |
| 7,524,404 B2 | 4/2009 | Boatman | |
| 7,569,039 B2 | 8/2009 | Matsuda et al. | |
| 7,971,526 B2 | 7/2011 | Blenke | |
| 8,196,630 B2 | 6/2012 | Busch | |
| 2003/0008109 A1 | 1/2003 | Basler | |
| 2003/0041953 A1 | 3/2003 | Farrell | |
| 2003/0046906 A1 | 3/2003 | Kume et al. | |
| 2004/0011107 A1 | 1/2004 | Boegli | |
| 2004/0097895 A1 | 5/2004 | Busam et al. | |
| 2004/0158212 A1 | 8/2004 | Ponomarenko et al. | |
| 2004/0216830 A1 | 11/2004 | Van Eperen | |
| 2004/0241399 A1 | 12/2004 | Marmon et al. | |
| 2005/0107764 A1 | 5/2005 | Matsuda et al. | |
| 2005/0257910 A1 | 11/2005 | Boatman | |
| 2006/0004334 A1 | 1/2006 | Schlinz | |
| 2006/0266473 A1 | 11/2006 | Senapati et al. | |
| 2007/0093157 A1 | 4/2007 | Shannon et al. | |
| 2007/0296104 A1 | 12/2007 | Shannon et al. | |
| 2009/0312730 A1 | 12/2009 | LaVon et al. | |
| 2010/0251911 A1 | 10/2010 | Nakata | |
| 2012/0061015 A1 | 3/2012 | LaVon et al. | |
| 2012/0061016 A1 | 3/2012 | LaVon et al. | |
| 2012/0157950 A1 | 6/2012 | Geilich | |
| 2013/0213547 A1 | 8/2013 | Schneider | |
| 2013/0255861 A1 | 10/2013 | Schneider | |
| 2013/0255862 A1 | 10/2013 | Schneider et al. | |
| 2013/0255863 A1 | 10/2013 | Schneider et al. | |
| 2013/0255865 A1 | 10/2013 | Dean et al. | |
| 2014/0377506 A1 * | 12/2014 | Eckstein | B29C 65/8223 428/161 |
| 2015/0173961 A1 | 6/2015 | Powell et al. | |

FOREIGN PATENT DOCUMENTS

| | | |
|---|---|---|
| JP | 2005/343541 | 12/2005 |
| JP | 2006-527102 | 11/2006 |
| JP | 2013-106912 | 6/2013 |
| WO | WO 2004/108037 A1 | 12/2004 |
| WO | WO 2009/082277 A1 | 7/2009 |
| WO | WO 2011/099297 A1 | 8/2011 |

OTHER PUBLICATIONS

U.S. Appl. No. 14/301,426, filed Jun. 11, 2014, Hailing Bao, et al.
U.S. Appl. No. 14/301,426, filed Jun. 11, 2014—Notice of Allowance dated Sep. 25, 2017 (8 pages).
U.S. Appl. No. 14/301,426, filed Jun. 11, 2014—Office Action dated Sep. 28, 2016 (6 pages).
U.S. Appl. No. 14/301,426, filed Jun. 11, 2014—Office Action dated May 5, 2016 (8 pages).

* cited by examiner

Fig. 10

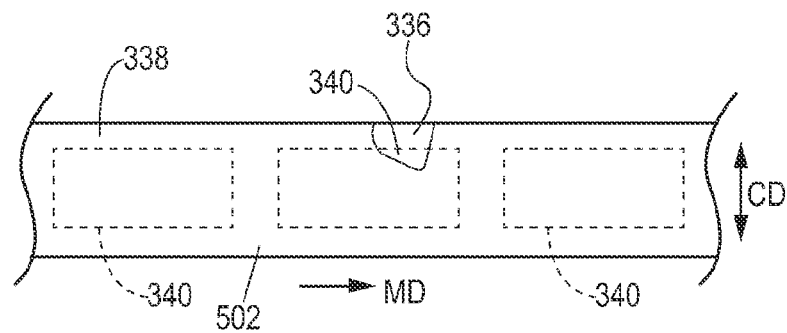
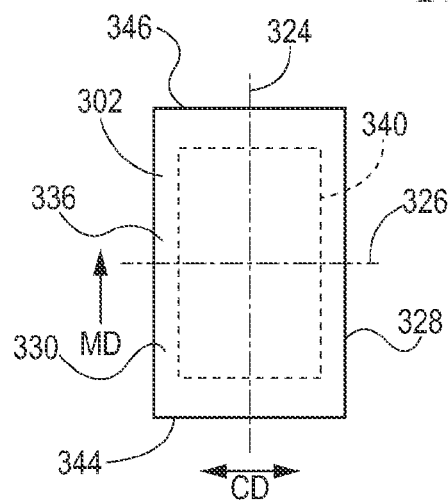
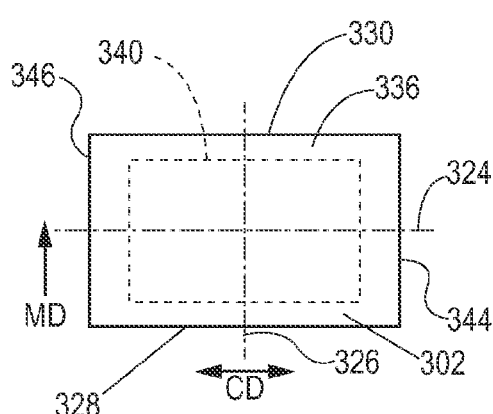
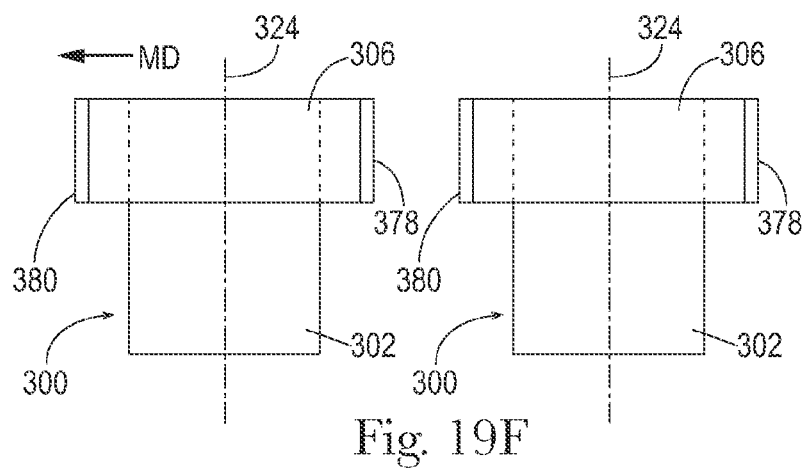

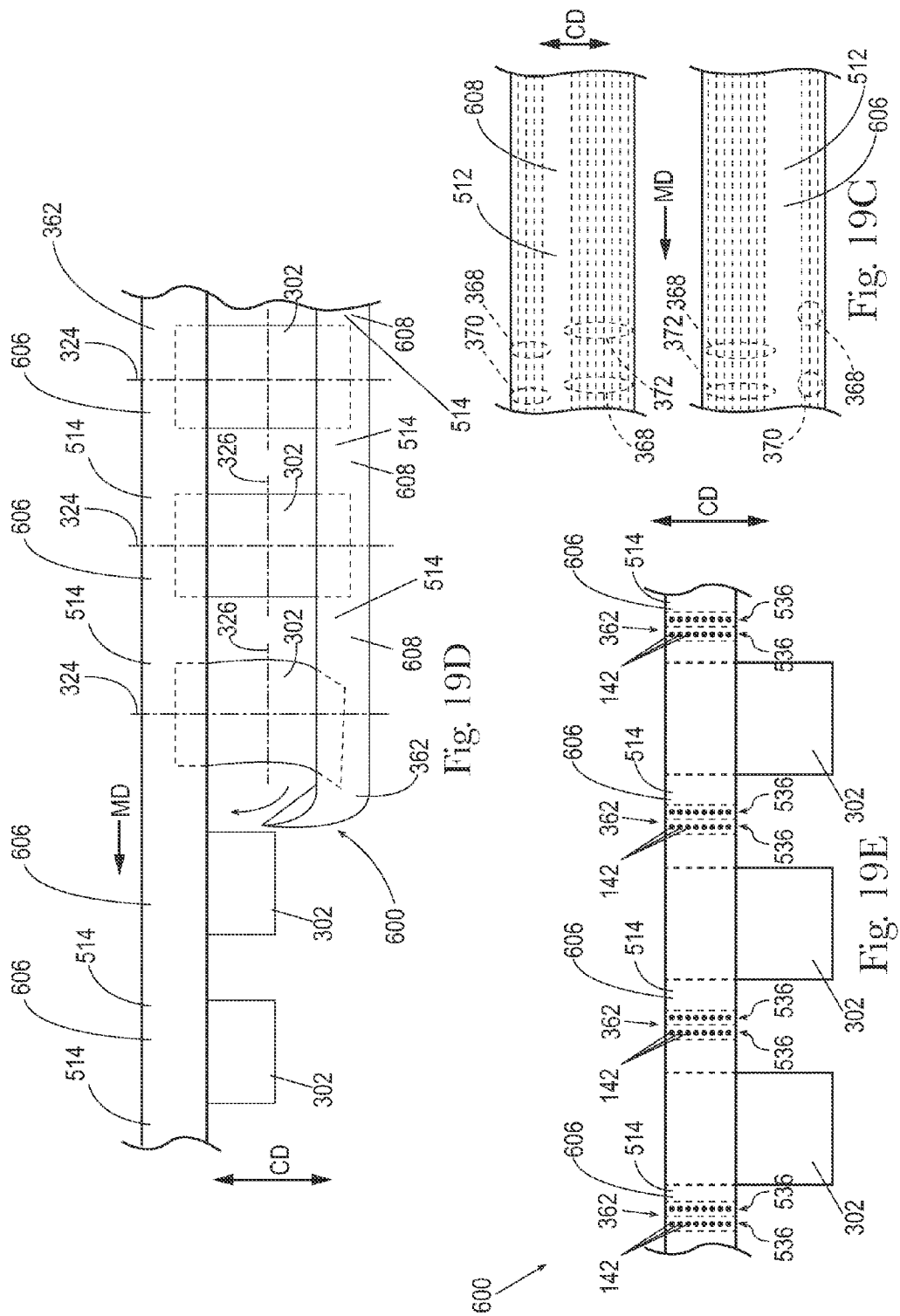

BONDING APPARATUS AND METHOD

CROSS REFERENCE TO RELATED APPLICATIONS

This application claims the benefit of U.S. Provisional Application 61/836,745, filed Jun. 19, 2013, which is hereby incorporated by reference.

FIELD OF THE INVENTION

The present disclosure relates to methods for manufacturing absorbent articles, and more particularly, to apparatuses and methods for bonding substrates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

During the assembly process, various components and/or advancing webs of material may be bonded together in various ways. For example, in some processes, advancing webs and/or components may be bonded together with adhesives. In other processes, advancing webs and/or components may be mechanically bonded together with heat and pressure without the use of adhesives. An example of such a mechanical bonding method and apparatus is disclosed in U.S. Pat. No. 4,854,984, wherein two laminae are bonded together by advancing through a nip between a patterned cylinder and an anvil cylinder. Pattern elements on the patterned cylinder exert pressure on the two laminae against the anvil roll to create discrete bond sites. More particularly, bond sites are created as the extreme nip pressure compresses and yields the laminae material in areas between the pattern elements and the anvil. During the bonding process, some of the yielded material may flow from the bond site to areas surrounding the perimeter of the pattern element.

However, extreme nip pressures may exceed the compressive yield strength of cold work powder metal tool steels. In addition, current mechanical bonding methods are susceptible to pattern element chipping, spalling, buckling, and/or otherwise fracturing, referred to generally as bond tool breakdown, sometimes necessitating frequent and costly repairs. These mechanical bonding methods may also damage the laminae by forming holes and/or tears in or around the bond sites. For example, pattern elements may become deformed and/or fail after prolonged use due to high stresses that occur in the center portions of the pattern element during the bonding operation. In some instances, such high stresses may cause craters to form in the bonding surfaces of pattern elements. As a pattern element degrades, the bonds created thereby may have inconsistent aesthetic appearances; have relatively weaker strengths; and may tear or cut the bonded laminae in areas adjacent to the bonds. In addition, as the web basis weight of laminae decreases, bonds may become more susceptible to bond defects such as tearing and pinholes at relatively high nip pressures.

Consequently, it would be beneficial to provide a method and apparatus for mechanically bonding substrates that produces bond sites with relatively low damage to the laminae and with reduced bond tool breakdown.

SUMMARY OF THE INVENTION

The present disclosure relates to methods and apparatuses for mechanically bonding substrates together. The apparatuses may include a pattern roll having three or more pattern elements protruding radially outward, wherein each pattern element includes a pattern surface. The pattern surfaces are also separated from each other by gaps having minimum widths. The pattern roll may be adjacent an anvil roll to define a nip between the pattern surfaces and the anvil roll, wherein the pattern roll is biased toward the anvil roll to define a nip pressure between pattern surfaces and the anvil roll. As substrates advance between the pattern roll and anvil roll, the substrates are compressed between the anvil roll and the pattern surfaces to form a discrete bond region between the substrates. During the bonding process, some of yielded substrate material also flows from under the pattern surfaces and into the gaps to form gap grommet regions.

In one embodiment, an apparatus for dynamically bonding substrates comprises: an anvil roll; a bonding roll including: base circumferential surface; a first pattern element including a first pattern surface having a first pattern area, A1, wherein A1 is greater than about 0.25 mm$^2$ and less than about 2.00 mm$^2$, wherein the first pattern element protrudes outward from the base circumferential surface to define a distance, Hp1, between the first pattern surface and the base circumferential surface, and wherein the first pattern element is bounded by a first perimeter; a second pattern element including a second pattern surface having a second pattern area, A2, wherein A2 is greater than about 0.25 mm$^2$ and less than about 2.00 mm$^2$, wherein the second pattern element protrudes outward from the base circumferential surface to define a distance, Hp2, between the second pattern surface and the base circumferential surface, and wherein the second pattern element is bounded by a second perimeter; and a third pattern element including a third pattern surface having a third pattern area, A3, wherein A3 is greater than about 0.25 mm$^2$ and less than about 2.00 mm$^2$, wherein the third pattern element protrudes outward from the base circumferential surface to define a distance, Hp3, between the third pattern surface and the base circumferential surface, and wherein the third pattern element is bounded by a third perimeter; wherein the first and second pattern surfaces are separated by a first gap having a minimum width, D1, wherein the first and third pattern surfaces are separated by a second gap having a minimum width, D2, and wherein the second and third pattern surfaces are separated by a third gap having a minimum width, D3, and wherein D1, D2, and D3 are greater than 0.20 mm and less than about 3.00 mm; and wherein the bonding roll is adjacent the anvil roll to define a nip between the first, second, and third pattern surfaces and the anvil roll; and wherein the bonding roll is biased toward the anvil roll to define a nip pressure of greater than about 40,000 PSI and less than about 60,000 PSI between each pattern surface and the anvil roll.

In another embodiment, a method of bonding substrates comprises the steps of: rotating an anvil roll; rotating a pattern roll adjacent the anvil roll, the pattern roll including a base circumferential surface, a first pattern element including a first pattern surface, a second pattern element including a second pattern surface, and a third pattern element including a third pattern surface; wherein each pattern surface defines an area, A, wherein A is greater than about 0.25 mm$^2$ and less than about 2.00 mm$^2$; wherein each pattern element protrudes outward from the base circumferential surface to define a distance, Hp, between the first, second, and third pattern surfaces and the base surface, and wherein each pattern element is bounded by a perimeter; wherein the first and second pattern surfaces are separated by a first gap having a minimum width, D1, wherein the first and third pattern surfaces are separated by a second gap having a minimum width, D2, and wherein the second and third pattern surfaces are separated by a third gap having a minimum width, D3, and wherein D1, D2, and D3 are greater than 0.20 mm and less than about 3.00 mm; biasing the bonding roll toward the anvil roll to define a nip pressure of greater than about 40,000 PSI and less than about 60,000 PSI between each pattern surface and the anvil roll; advancing a first substrate and a second substrate in a machine direction between the pattern roll and the anvil roll; and compressing the first substrate and the second substrate between the anvil roll and the first, second, and third pattern surfaces to form a discrete bond region between the first and second substrates.

In yet another embodiment, a laminate comprises: a first substrate comprising nonwoven fibers; a second substrate comprising nonwoven fibers; a discrete bond between the first substrate and the second substrate, the discrete bond comprising: a first membrane region comprising nonwoven fibers of the first and second substrates that have been yielded under pressure and are fused together, defining a first area, A1, greater than about 0.25 mm$^2$ and less than about 2.00 mm$^2$; a second membrane region comprising nonwoven fibers of the first and second substrates that have been yielded under pressure and are fused together, defining a second area, A2, greater than about 0.25 mm$^2$ and less than about 2.00 mm$^2$; a third membrane region comprising nonwoven fibers of the first and second substrates that have been yielded under pressure and are fused together, defining a third area, A3, greater than about 0.25 mm$^2$ and less than about 2.00 mm$^2$; a first gap grommet region separating the first membrane region and the second membrane region, wherein the first gap grommet region comprises material of the first and second substrates that has been transferred from the first membrane region and second membrane region, and wherein the first gap grommet region defines a minimum width, D1, that is greater than 0.20 mm and less than about 3.00 mm; a second gap grommet region separating the first membrane region and the third membrane region, wherein the second gap grommet region comprises material of the first and second substrates that has been transferred from the first membrane region and third membrane region, wherein the second gap grommet region defines a minimum width, D2, that is greater than 0.20 mm and less than about 3.00 mm; a third gap grommet region separating the second membrane region and third membrane region, wherein the third gap grommet region comprises material of the first and second substrates that has been transferred from the second membrane region and the third membrane region, wherein the third gap grommet region defines a minimum width, D3, that is greater than 0.20 mm and less than about 3.00 mm; an outer grommet region partially surrounding the first membrane region, wherein the outer grommet region comprises material of the first and second substrates that has been transferred from the first membrane region.

BRIEF DESCRIPTION OF THE DRAWINGS

FIG. 10 is a detailed side view along the machine direction MD of the second and third pattern elements of FIG. 5 bonding a first substrate with a second substrate.

FIG. 19A is a view of a continuous length of chassis assemblies from FIG. 18 taken along line A-A.

FIG. 19B1 is a view of a discrete chassis from FIG. 18 taken along line B1-B1.

FIG. 19B2 is a view of a discrete chassis from FIG. 18 taken along line B2-B2.

FIG. 19C is a view of continuous lengths of advancing front and back side panel material from FIG. 18 taken along line C-C.

FIG. 19D is a view of multiple discrete chassis spaced from each other along the machine direction MD and connected with each other by the front and back side panel material from FIG. 18 taken along line D-D.

FIG. 19E is a view of folded multiple discrete chassis with the front and back side panel material in a facing relationship from FIG. 18 taken along line E-E.

FIG. 19F is a view of two discrete absorbent articles advancing the machine direction MD from FIG. 18 taken along line F-F.

DETAILED DESCRIPTION OF THE INVENTION

Figure 1:
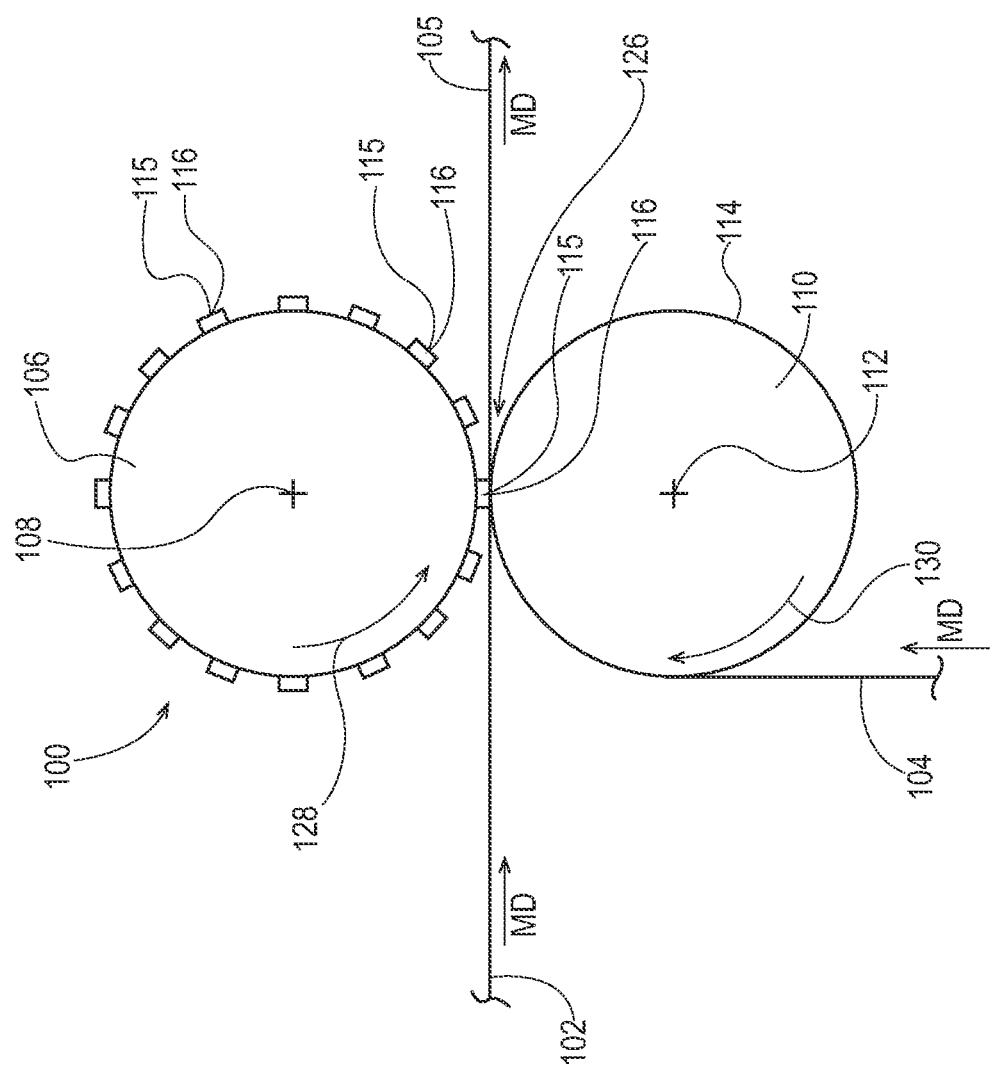
FIG. 1 is a schematic side view of a bonding apparatus.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "yield" is used herein to refer to permanent and non-reversible material displacement due to subjecting the material to mechanical stress past the yield stress of the material and/or permanent and non-reversible material displacement due to subjecting the material to temperatures higher than the melting point of the material.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods and apparatuses for manufacturing absorbent articles, and in particular, to methods and apparatuses for mechanically bonding substrates together. The apparatuses may include a pattern roll and an anvil roll. The pattern roll may include three or more pattern elements protruding radially outward, wherein each pattern element includes a pattern surface. And the pattern roll may be adjacent the anvil roll to define a nip between the pattern surfaces and the anvil roll, wherein the pattern roll is biased toward the anvil roll to define a nip pressure between pattern surfaces and the anvil roll. As the first and second substrates advance between the pattern roll and anvil roll, the first substrate and the second substrate are compressed between the anvil roll and the pattern surfaces to form a discrete bond region between the first and second substrates. More particularly, during the bonding process, heat generated by the nip pressure causes the first and second substrate material to yield. And the yielded material is pressed together to form a bond region. In addition, some of the yielded material flows outward from under the pattern surfaces to form one or more outer grommet regions along the outer perimeter of one or more pattern elements. As discussed in more detail below, the pattern surfaces are also separated from each other by gaps having minimum widths. As such, during the bonding process, some of the yielded material also flows from under the pattern surfaces and into the gaps to form gap grommet regions.

It is to be appreciated that various arrangements and configurations of the apparatuses and methods herein may be used to bond various types of substrates together. For example, as discussed in more detail below, apparatuses and methods according to the present disclosure may be utilized to bond various substrates together during the production of various components of absorbent articles, such as diapers.

Figure 2:
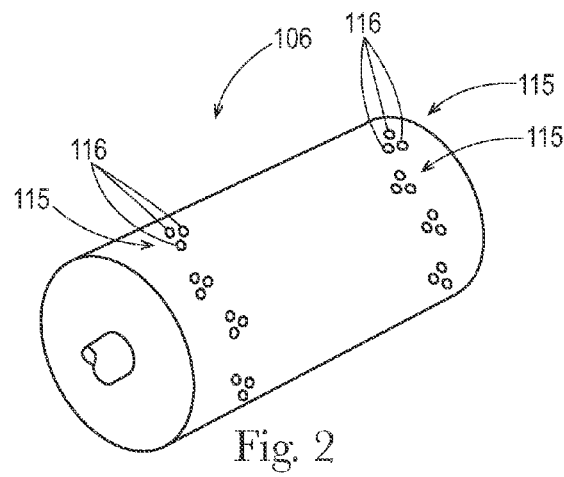
FIG. 2 is a detailed view of the bonding apparatus of FIG. 1.
Figure 3:
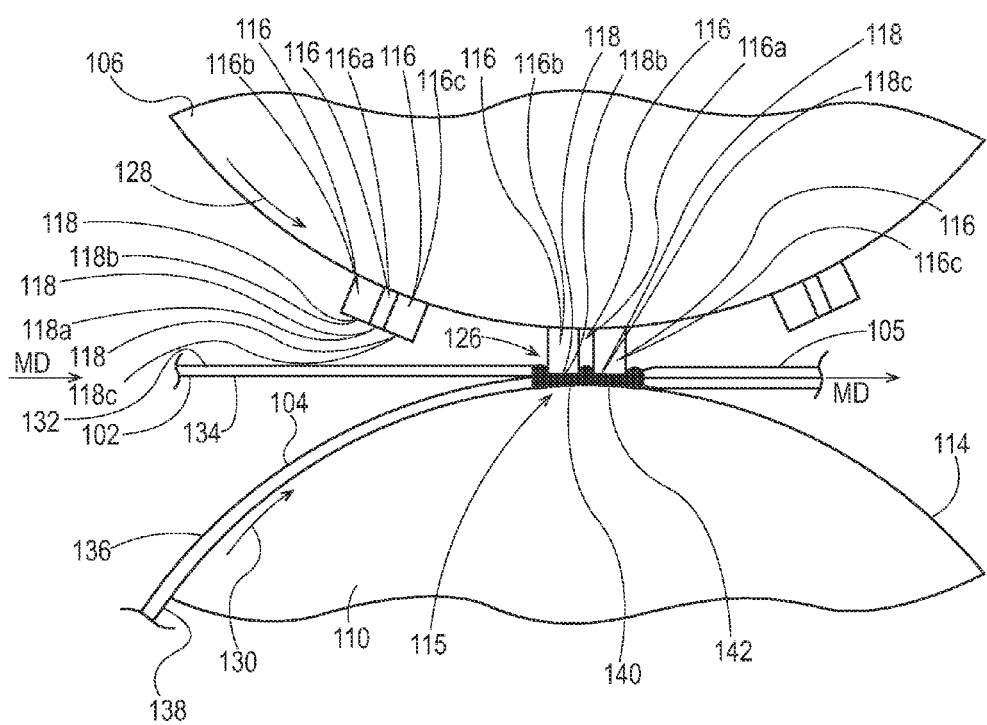
FIG. 3 is a perspective view a pattern roll.
Figure 4:
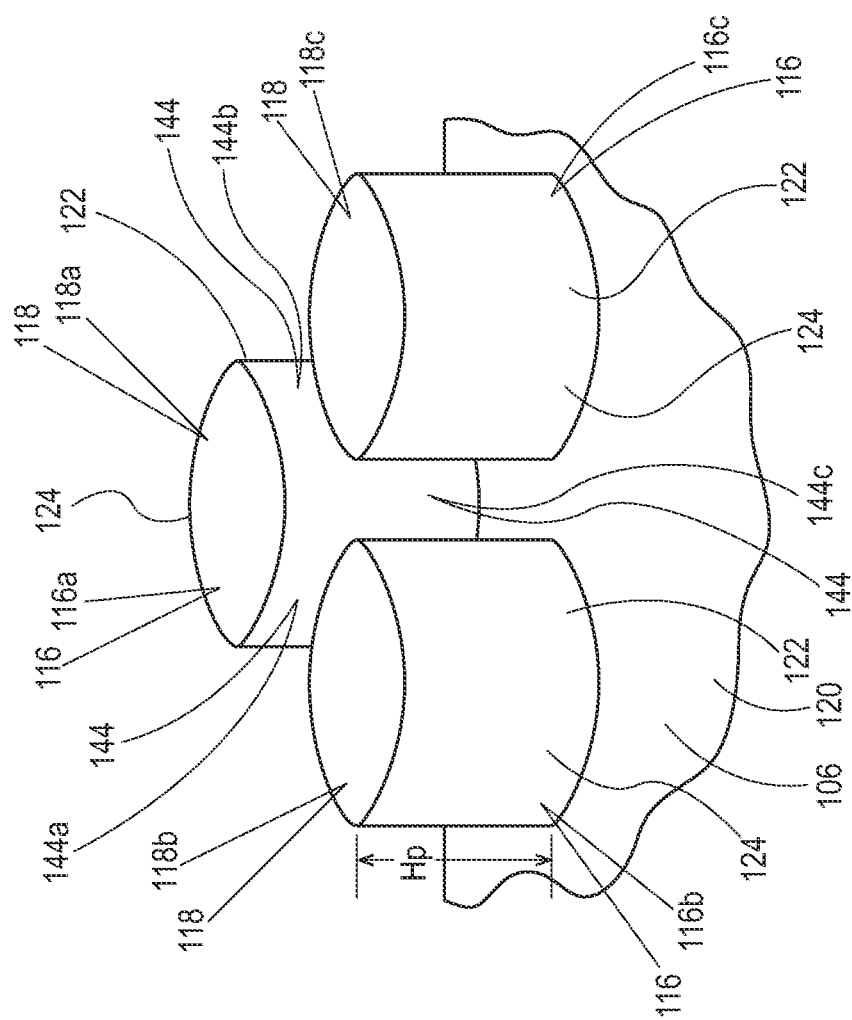
FIG. 4 is a detailed isometric view of three pattern elements.

FIG. 1 shows an embodiment of a bonding apparatus 100 that may be used to bond a first substrate 102 and a second substrate 104 together to form a laminate 105. As shown in FIG. 1, the bonding apparatus 100 may include a bonding roll 106, also referred to herein as a pattern roll 106, adapted to rotate around an axis of rotation 108, and an anvil roll 110 adapted to rotate around an axis of rotation 112. The anvil roll 110 includes an outer circumferential surface 114. And as shown in FIGS. 1-4, the pattern roll 106 may include one or more groupings 115 of pattern elements 116, each pattern element 116 including a pattern surface 118. With particular reference to FIG. 4, the pattern roll 106 may include a base circumferential surface 120, wherein each pattern element 116 includes a circumferential wall 122 that protrudes radially outward from the base circumferential surface 120 to define a distance, Hp, between the pattern surface 118 and the base surface 120. The circumferential wall 122 also defines an outer perimeter 124 of the pattern element 116. It is to be appreciated that in some embodiments, the circumferential wall 122 may be perpendicular to base circumferential surface 120 or may sloped or tapered with respect to the base circumferential surface 120. As shown in FIGS. 1 and 2, the pattern roll 106 is adjacent the anvil roll 110 so as to define a nip 126 between the pattern roll 106 and the anvil roll 110, and more particularly, to define a nip 126 between the pattern surface 118 of each pattern element 116 and the anvil roll 110. As discussed in more detail below, the pattern roll 106 may be biased toward the anvil roll 110 to define a nip pressure between the pattern surface 118 and the anvil roll 106. It is to be appreciated that the anvil roll 110 may also be biased toward the pattern roll 106, and/or the pattern and anvil rolls may be biased toward each other to define the nip pressure between the pattern surface 118 and the anvil roll 110. It is to be appreciated that the pattern roll 106 and the anvil roll 110 may be configured to rotate such that the pattern surfaces 118 on the pattern roll 106 and the outer circumferential surface 114 of the anvil roll 110 move at the same speeds or different speeds. It is to be appreciated that the bonding methods and apparatuses herein can be configured to bond substrates together that are advancing at various speeds, such as for example, speeds of about 240 feet or more per minute.

As shown in FIGS. 1 and 2, during the bonding operation, the pattern roll 106 may rotate in a first direction 128 around the axis of rotation 108 of the pattern roll 106, and the anvil roll 110 may rotate in a second direction 130, opposite the first direction 128, around the axis of rotation 112 of the anvil roll 110. The first substrate 102 and second substrate 104 may advance in a machine direction MD between the pattern roll 106 and the anvil roll 110. More particularly, the first substrate 102 includes a first surface 132 and a second surface 134 opposite the first surface 132, and the second substrate 104 includes a first surface 136 and a second surface 138 opposite the first surface 136. As such, the first surface 132 of the first substrate 102 is contacted by the pattern roll 106, and the second surface 138 of the second substrate 104 is contacted by the anvil roll 110. And the second surface 134 of the first substrate 102 and the first surface 136 of the second substrate 104 contact each other. As first substrate 102 and second substrate 104 advance through the nip 126 between the pattern surface 118 of a pattern element 116 and the anvil roll 110, the pattern element 116 contacts the first substrate 102 and compresses the first substrate 102 and second substrate 104 between the pattern surface 118 of the pattern element 116 and the anvil roll 110. In turn, heat generated by the nip pressure causes the first and second substrate material to yield. And, as described below with reference to FIGS. 8-10, the pattern surface 118 presses yielded material 140 of the first and second substrates 102, 104 together to form a discrete bond region 142 between the first and second substrates 102, 104. Thus, the apparatus 100 may form a laminate 105 including first and second substrates 102, 104 bonded together by discrete bond regions 142, without the use of adhesives. It is to be appreciated, however, that the bonding apparatus 100 may also be used in combination with adhesives. Although FIG. 1 shows the apparatus 100 bonding two substrates together, it is to be appreciated that the apparatus may bond more than two substrates together. In addition, it is to be appreciated that the apparatus may also be used to bond fibers of nonwoven together on a single substrate and/or emboss a pattern on a single substrate. It should also be appreciated that the pattern elements 116 may be configured with the same or different distances, Hp, between the pattern surface 118 and the base surface 120. In addition, the distance, Hp, may be greater than the sum of the thicknesses of the substrates 102, 104 being bonded.

It is to be appreciated that various pattern element configurations may be used with the bonding apparatuses and processes herein. Various quantities pattern elements may be arranged in groupings to form discrete bonds. For example, FIGS. 3-7 show a grouping 115 of pattern elements 116 with pattern surfaces 118 separated by gaps 144. The gaps 144 between the pattern elements provide a location, in addition to regions outside of and adjacent to the perimeter 124 of the pattern element 116, for yielded substrate material 140 to flow during the bonding process. Allowing yielded substrate material 140 to flow to the gaps 144 during the bonding process may help provide stress relief on the pattern element 116, which may in turn, help reduce the frequency of pattern element deformations, including buckling, and/or failures and may help provide for more relatively more consistent and stronger bonds.

With continued reference back to FIGS. 4-7, the grouping 115 of pattern elements 116 may include a first pattern element 116a including a first pattern surface 118a; a second pattern element 116b including a second pattern surface 118b; and a third pattern element 116c including a third pattern surface 118c. The first pattern element 116a protrudes radially outward from the base circumferential surface 120 to define a distance, Hp1, between the first pattern surface 118a and the base surface 120. The second pattern element 116b protrudes radially outward from the base circumferential surface 120 to define a distance, Hp1, between the second pattern surface 118b and the base surface 120. The third pattern element 116c protrudes radially outward from the base circumferential surface 120 to define a distance, Hp3, between the third pattern surface 118c and the base surface 120. It is to be appreciated that the distances Hp1, Hp2, and/or Hp3 may be the same or different. Embodiments that are configured with distances Hp1, Hp2, and/or Hp3 are different may utilize bearer ring configurations such as described in European Patent Publication No. EP1635750B1.

Although the grouping 115 of pattern elements 116 is depicted as including three pattern elements, it is to be appreciated that groupings may include more than three pattern elements. As shown in FIG. 4, the first pattern surface 118a and the second pattern surface 118b are separated by a first gap 144a; the first pattern surface 118a and the third pattern surface 118c are separated by a second gap 144b; and the second pattern surface 118b and the third pattern surface 118c are separated by a third gap 144c. The first gap 144a may define a minimum width, D1; the second gap 144b may define a minimum width, D2; and the third gap 144c may define a minimum width, D3. As such, the first pattern surface 118a may be separated from the second and third pattern surfaces 118b, 118c by minimum distances of D1 and D2, respectively. And the second and third pattern surfaces may be separated from each other by the minimum distance, D3. The pattern elements may be arranged to also include gaps of various sizes. In some instances, the minimum widths (D1, D2, D3) of the gaps 144 may be greater than 0.20 mm and less than about 3.00 mm. In some embodiments, the minimum widths D1, D2, and/or D3 of the gaps 144 may be about 0.30 mm. It is to be appreciated that in some pattern element groupings, the gap widths D1, D2, and/or D3 may be the same or different.

Figure 5:
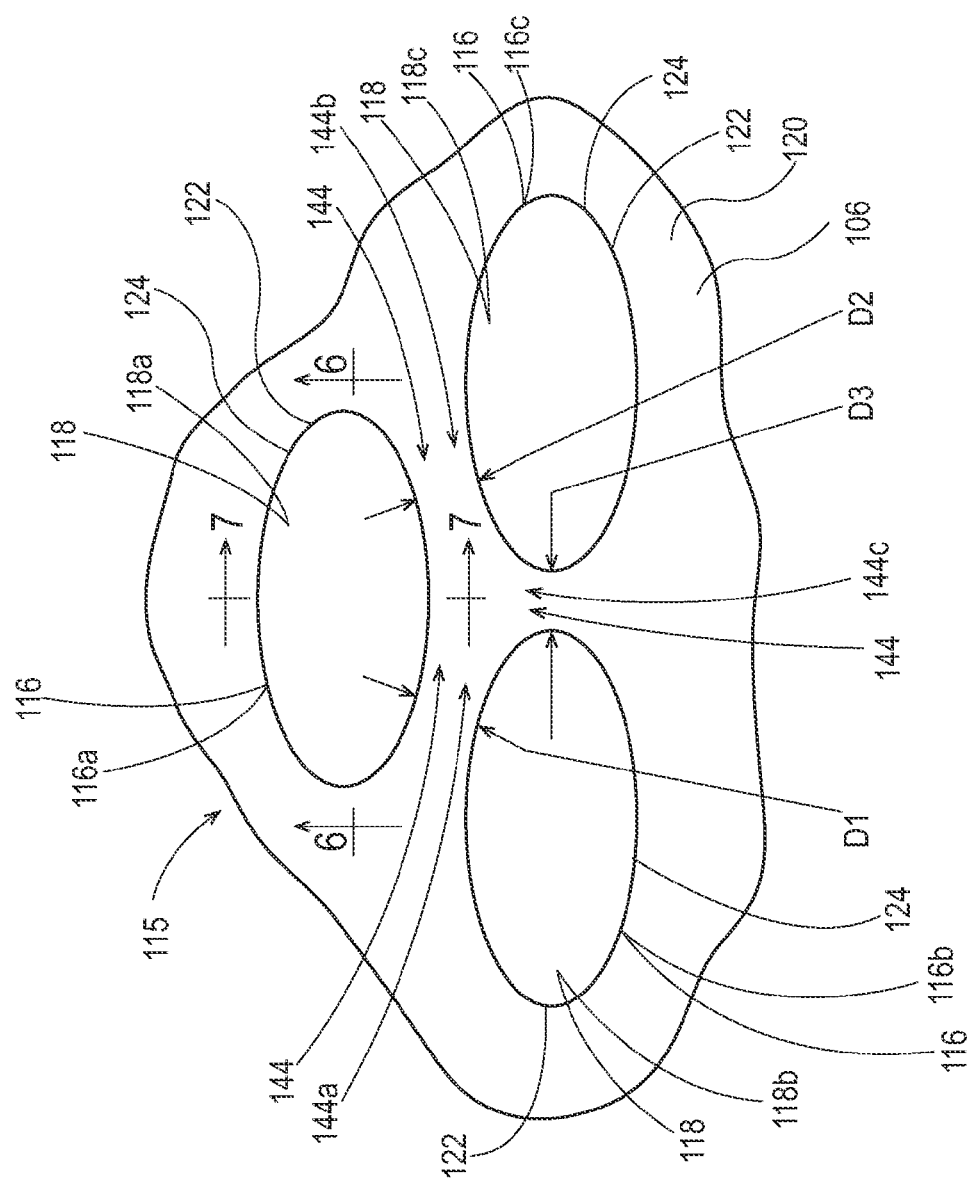
FIG. 5 is a top side view of the pattern elements of FIG. 4.
Figure 6:
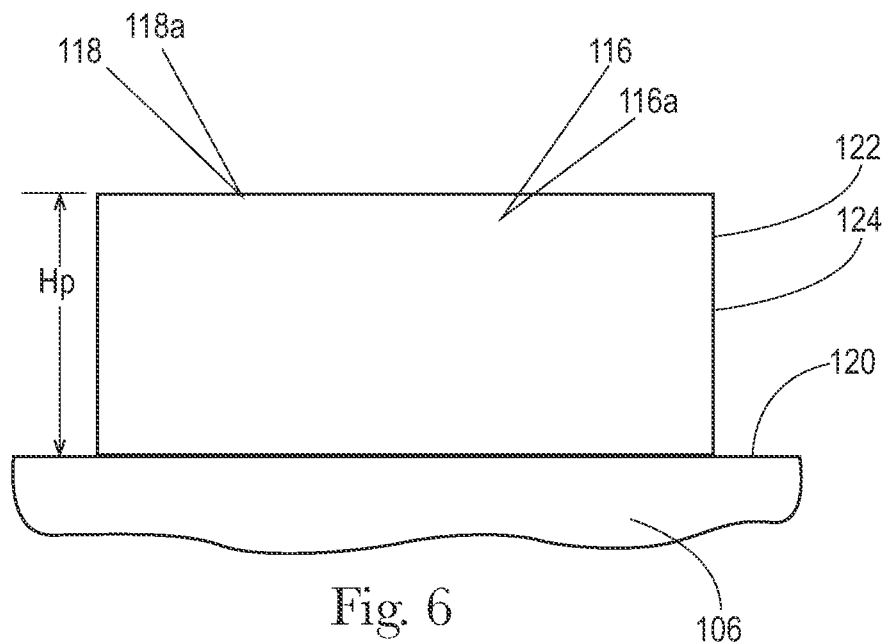
FIG. 6 is a cross-sectional view of a pattern element of FIG. 5 taken along line 6-6.
Figure 7:
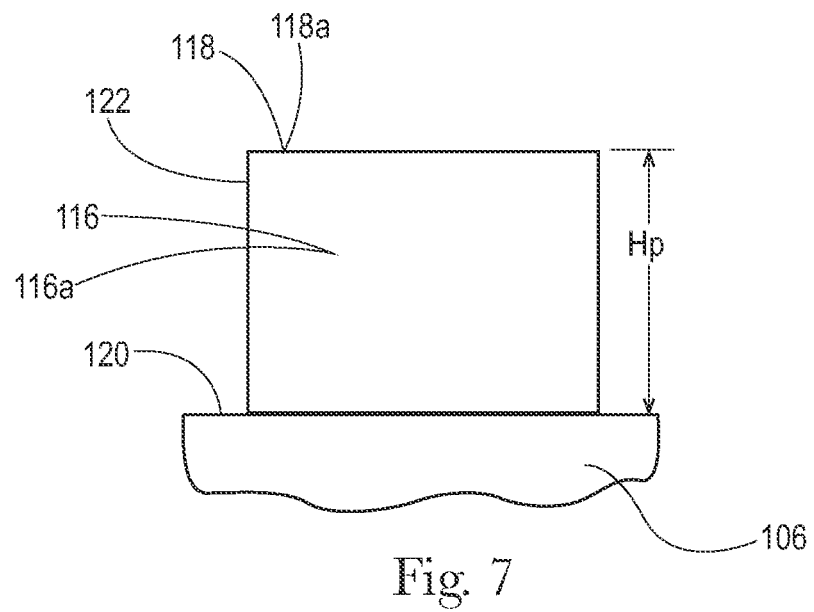
FIG. 7 is a cross-sectional view of a pattern element of FIG. 5 taken along line 7-7.

It is to be appreciated that the apparatus 100 may also be configured with various different configurations of pattern elements 116. For example, the first pattern surface 118a may define a first area, A1; the second pattern surface 118b may define a second pattern area, A2; and the third pattern surface may define a third pattern area, A3. As such, the pattern elements may be configured to also include pattern areas A of various sizes. In some instances, the pattern areas (A1, A2, A3) may be greater than about 0.25 mm$^2$ and less than about 2.00 mm$^2$. In some embodiments, pattern areas A1, A2, and/or A3 may be about 0.70 mm$^2$. It is to be appreciated that in some pattern element groupings, the pattern areas A1, A2, and/or A3 may be the same or different. In other examples, the pattern roll may be configured with pattern elements having different sizes and shapes. For example, in some embodiments, the pattern elements may have a perimeter that defines circular, square, rectangular, and various types of other shapes. For example, the pattern elements may have a perimeter that defines an elliptical shape, such as shown in FIG. 5. As such, in some embodiments, an elliptically shaped pattern element may have a major axis of about 1.27 mm and minor axis of about 0.56 mm. In some instances, the pattern elements may be configured such that resulting bond regions also offer aesthetic benefits such as, for example, a stitched like appearance along with a relatively smooth texture feel to the skin.

Figure 8:
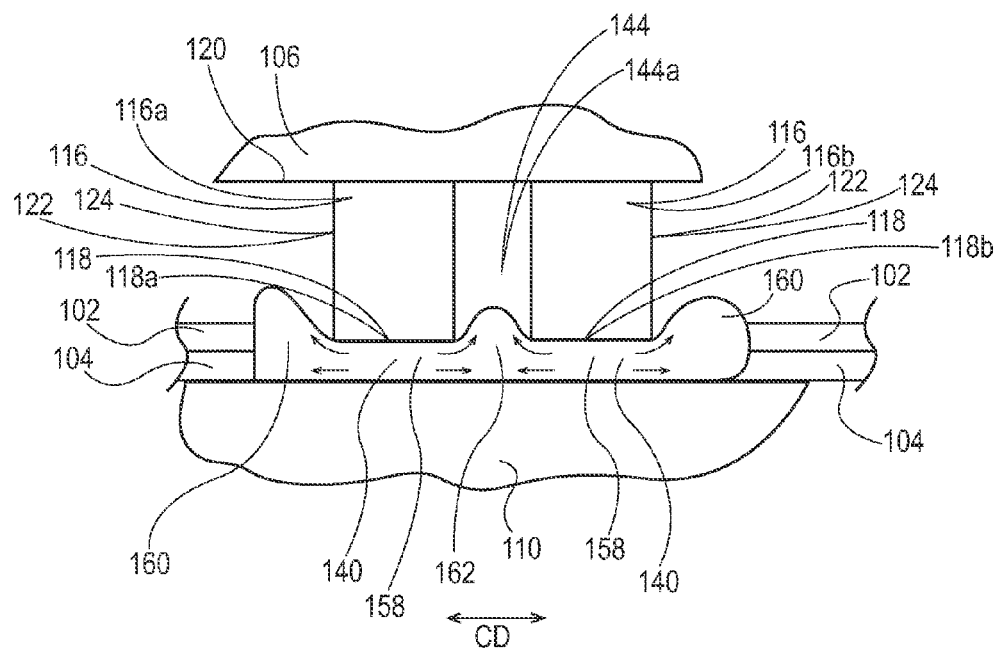
FIG. 8 is a detailed side view along the cross direction CD of the first and second pattern elements of FIG. 5 bonding a first substrate with a second substrate.
Figure 9:
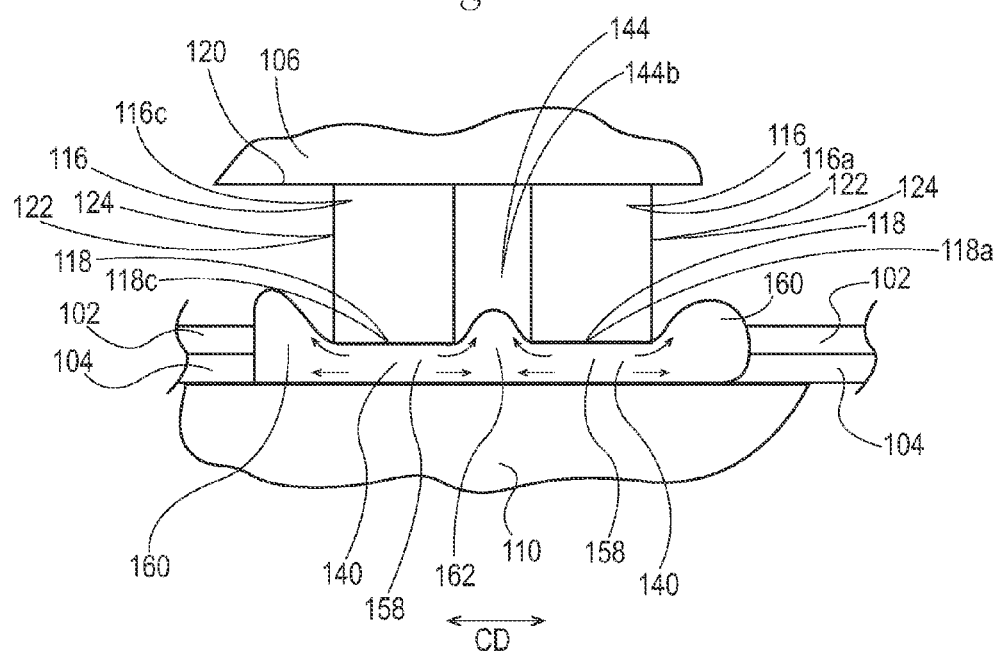
FIG. 9 is a detailed side view along the cross direction CD of the first and third pattern elements of FIG. 5 bonding a first substrate with a second substrate.
Figure 10:
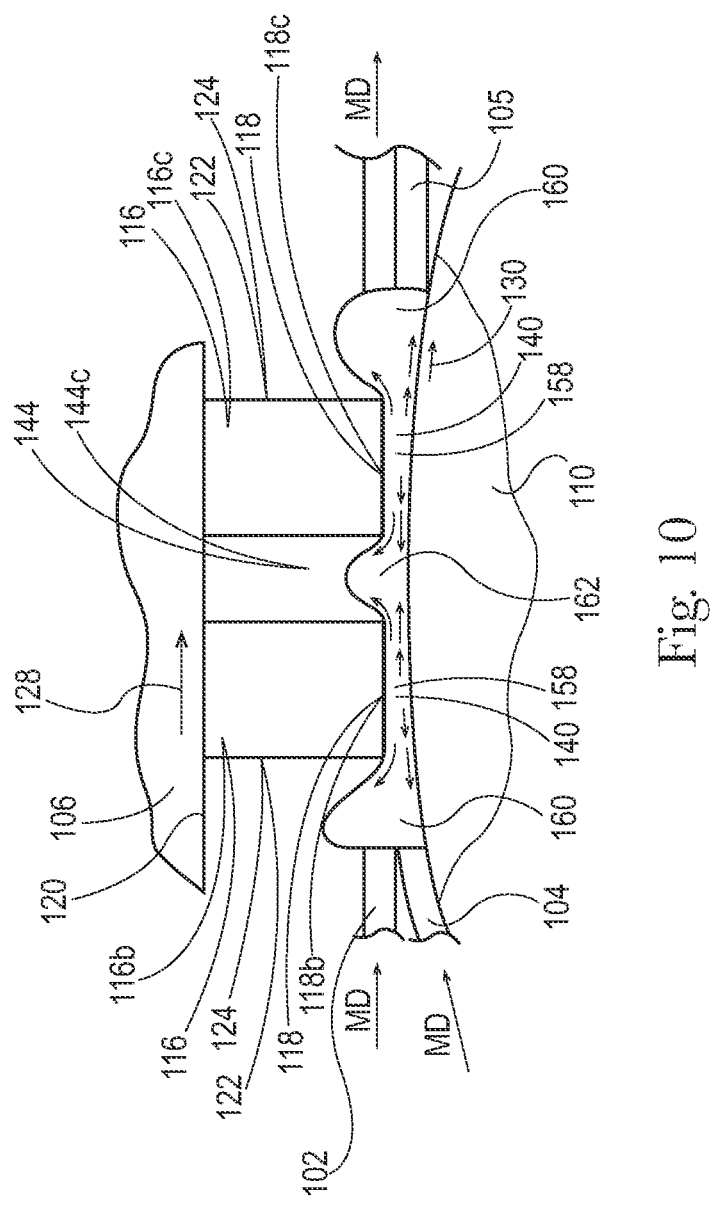

As discussed above, during the bonding process, the first and second substrates 102, 104 advance in the machine direction MD between the rotating pattern roll 106 and the anvil roll 110. As the pattern roll 106 and the anvil rotate 110, the pattern surfaces 118 of the pattern elements 116 contact the first substrate 106 and compress the first and second substrates 102, 104 in the nip 126 between the pattern surface 118 and the outer circumferential surface 114 of the anvil roll 112. Nip pressure between the pattern surface 118 of the pattern element 116 and the anvil roll 110 exerted on the first and second substrates 102, 104 causes some material 140 of the first and second substrates 102, 104 to yield. As shown in FIGS. 8-10, some of the yielded material 140 between the pattern surfaces 118a, 118b, 118c and the anvil roll 110 is fused together in first locations 158 between the pattern surfaces 118a, 118b, 118c and the anvil roll 110. In addition, some of the yielded material 140 flows out from between the pattern surfaces 118a, 118b, 118c and the anvil roll 110 to second locations 160 along the perimeter 124 of the pattern element 116. And some of the yielded material 140 flows out from between the pattern surfaces 118a, 118b, 118c and the anvil roll 110 to third locations 162 along the gaps 144a, 144b, 144c. As discussed in more detail below, the yielded material 140 in the first locations 158, second locations 160, and third locations 162 fuses together to form a discrete bond 142 between the first substrate 102 and the second substrate 104. More particularly, the yielded material 140 in the first locations 158 fuses together to form membrane regions 164 of the bond 142; the yielded material 140 in the first locations 160 fuses together to form outer grommet regions 166 of the bond 142; and the yielded material 140 in the third locations 162 fuses together to form gap grommet regions 168 of the bond 142.

Figure 11:
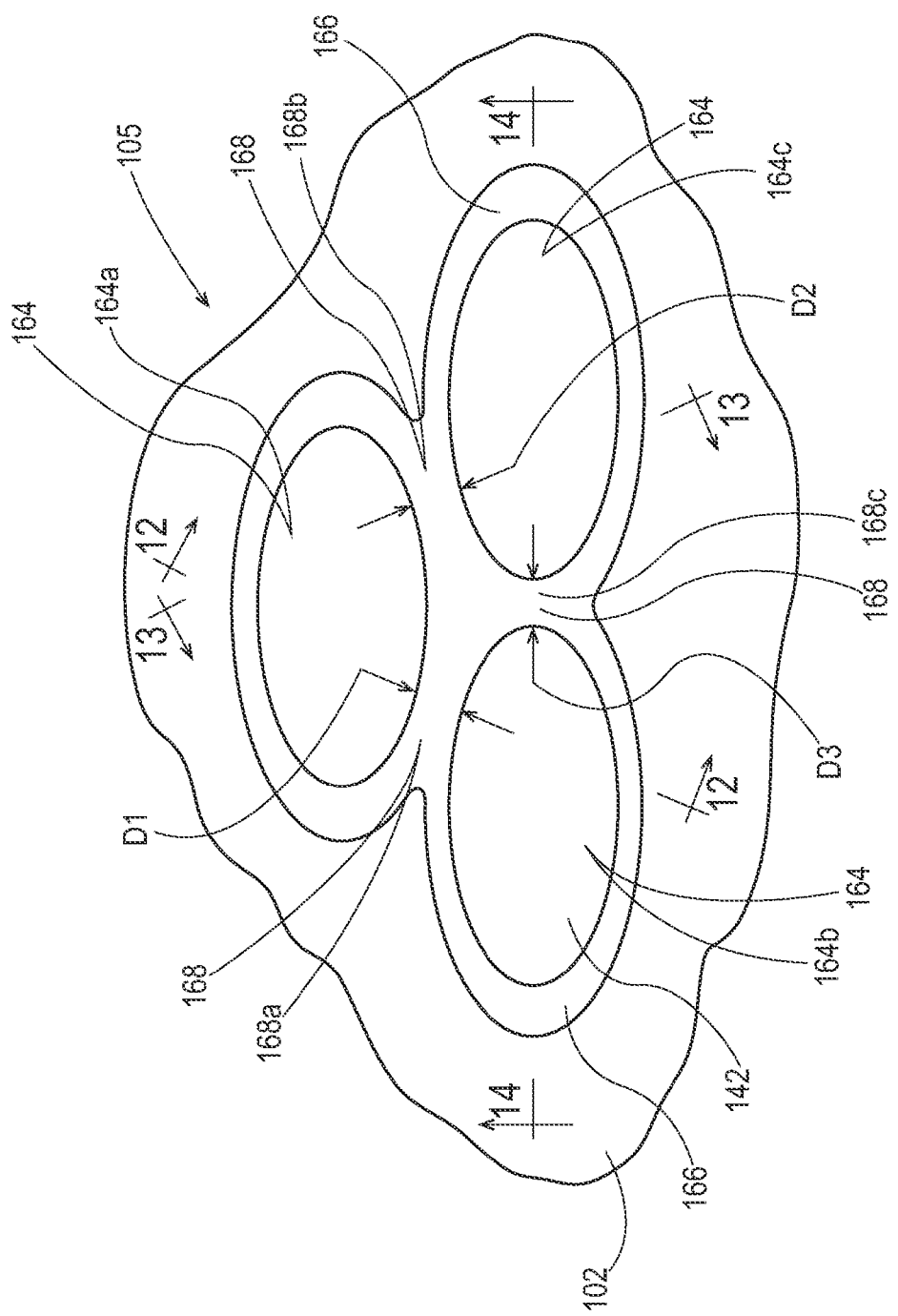
FIG. 11 is a top side view of a perspective view of a discrete bond region.

FIGS. 11-14 show an example bond 142 between the first and second substrates 102, 104 that may be created by the apparatus 100. As shown in FIG. 11, the bond 142 includes first regions 164, also referred to as membrane regions 164, that correspond with the first locations 158 wherein some of the yielded material 140 between the pattern surfaces 118 and the anvil roll 110 is fused together between the pattern surfaces 118 and the anvil roll 110. In particular, the bond 142 may include three membrane regions 164a, 164b, 164c that correspond with the pattern surfaces 118a, 118b, 118c, respectively. The bond 142 also includes second regions 166, also referred to as outer grommet regions 166, that correspond with the second locations 160 where some of the yielded material 140 that flowed out from between the pattern surfaces 118 and the anvil roll 110 to areas along the perimeter 124 of the pattern element 116 is fused together. In addition, the bond 142 includes third regions 168, also referred to as gap grommet regions 168, that correspond with the third locations 162 where some of the yielded material 140 that flowed out from between the pattern surfaces 118 and the anvil roll 110 to areas along the gaps 144 of the pattern element 116 is fused together. In some embodiments, the bond 142 may include three gap grommet regions 168a, 168b, 168c that correspond with the first, second, and third gaps 144a, 144b, 144c, respectively. As such, the outer region 166 may define a perimeter of the discrete bond 142, the perimeter surrounding a central region of the discrete bond 142 wherein the membrane regions 164 and the gap grommet regions 168 are located inside the central region.

As previously mentioned, the gaps 144 separating the pattern element provide locations, in addition to regions outside of and adjacent to the perimeters 124 of the pattern elements 116, for yielded substrate material 140 to flow and form gap and outer grommet regions during the bonding process. In contrast, when bonding substrates with pattern elements having relatively large pattern areas, yielded substrate material may be required to flow relatively longer distances to form perimeter grommet regions outside of and adjacent the perimeter of the pattern element. Stated another way, when bonding substrates with pattern elements having relatively small pattern areas, yielded substrate material may be required to flow relatively shorter distances to form gap grommet and outer grommet regions. The relatively shorter flow distances of yielded material may also help reduce hydraulic-like reactionary pressures in the nip. Further, some air may be entrained in substrates during formation, and collapse of the air bubbles, known as cavitation, may be significantly reduced by shortening the flow distance path needed for grommet formation.

Figure 20:
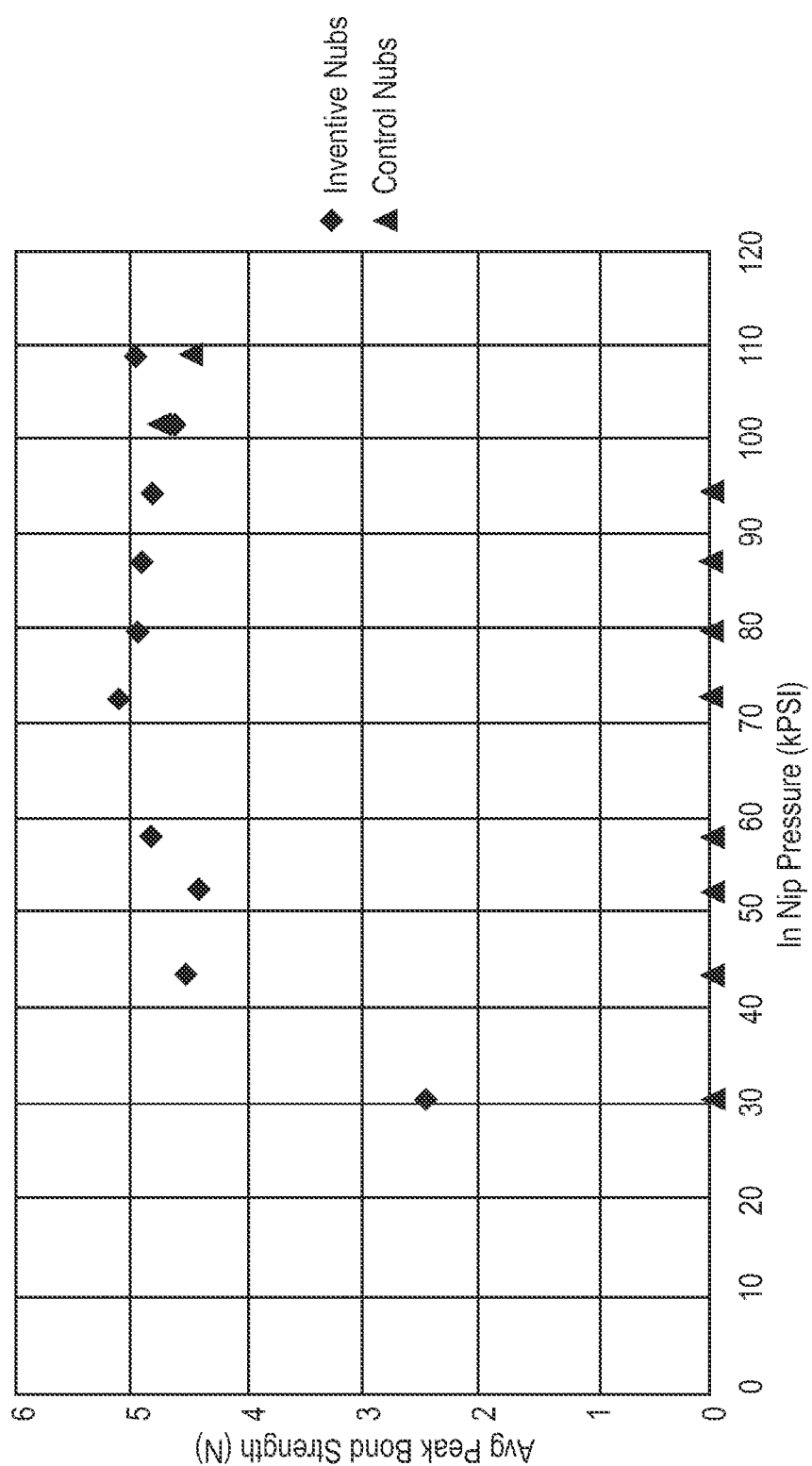
FIG. 20 is a graphical representation illustrating strengths of discrete bonds created by relatively small pattern element groupings and relatively large pattern element groupings over a range of pattern surface pressures.
Figure 21B:
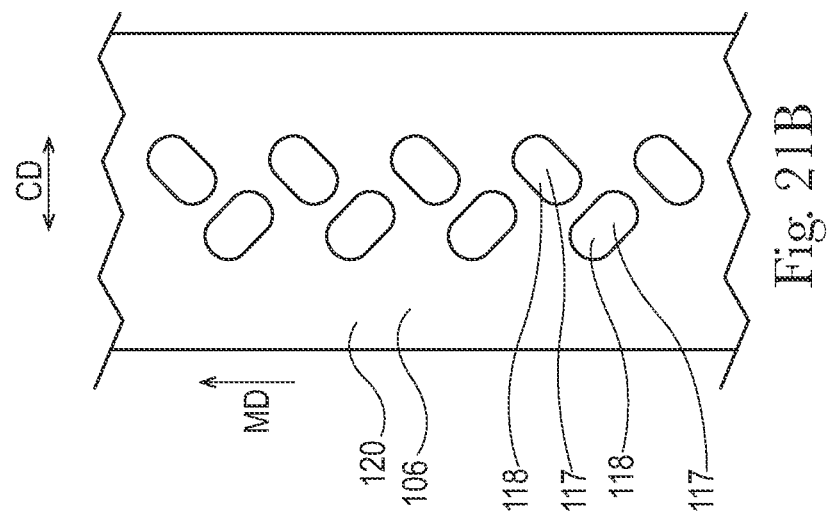
FIG. 21B illustrates the pattern element orientation of the Control Nubs on a pattern roll in the machine direction MD and cross direction CD.
Figure 21A:
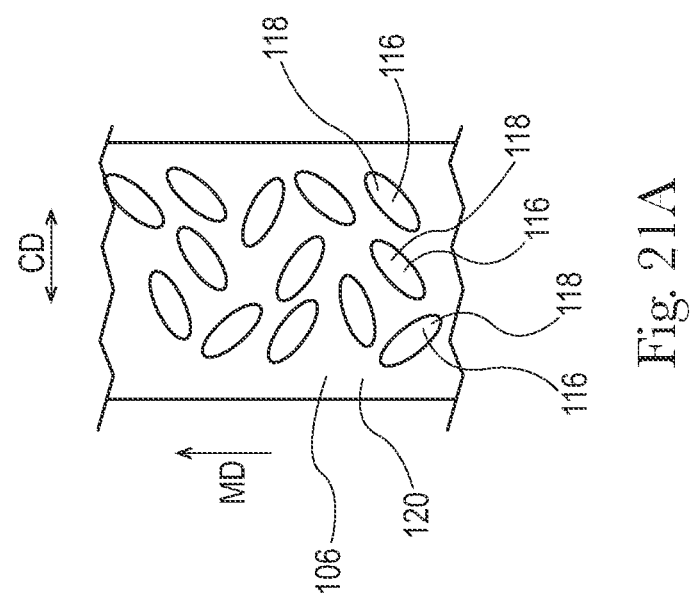
FIG. 21A illustrates the pattern element orientation of the Inventive Nubs on a pattern roll in the machine direction MD and cross direction CD.

It is also to be appreciated that the grouping 115 of pattern elements 116, such as shown in FIGS. 4-7, may create discrete bonds 142 having substantially the same bond strengths as discrete bonds created by pattern elements of a larger size and separated by large gaps with reduced nip pressures. For example, FIG. 20 provides a graph illustrating strengths of discrete bonds created by relatively small pattern element grouping and relatively large pattern element groupings over a range of nip pressures between the pattern surfaces and the anvil roll. In generating the data represented in FIG. 20, a 15 gsm polypropylene nonwoven substrate was bonded to a 12 gsm polypropylene nonwoven substrate with oval shaped, relatively small, pattern element groupings (Inventive Nubs 116). In addition, a 15 gsm polypropylene nonwoven substrate was bonded to a 12 gsm polypropylene nonwoven substrate with oval shaped, relatively large, pattern element groupings (Control Nubs 117). FIG. 21A illustrates the pattern element orientation of the Inventive Nubs on a pattern roll in the machine direction MD and cross direction CD. And FIG. 21B illustrates the pattern element orientation of the Control Nubs on a pattern roll in the machine direction MD and cross direction CD.

TABLE 1

| Pattern Element Grouping | Major Axis | Minor Axis | MD Distance between Pattern Surfaces | CD Distance Between Pattern Surfaces |
|---|---|---|---|---|
| Inventive Nubs | 1.27 mm | 0.56 mm | 0.31 mm | 0.31 mm |
| Control Nubs | 2.18 mm | 1.40 mm | 3.54 mm | 1.82 mm |

Table 1 above provides additional dimensional information about the oval-shaped Inventive Nub Grouping and the Control Nub Grouping used to generate the data illustrated in FIG. 20. The nonwoven substrates were bonded to each other with the Inventive Nubs and Control Nubs at various nip pressures between pattern surface and the anvil roll. The Average Peak Bond Strengths of the bonds generated at the various nip pressures were then measured according to the Peel Strength Test Method herein.

Figure 12:
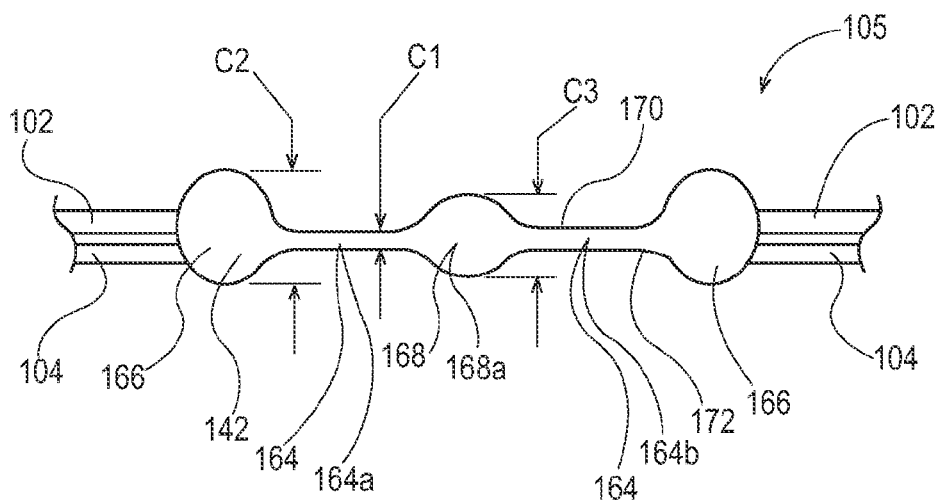
FIG. 12 is a cross-sectional view of the bond region of FIG. 11 taken along line 12-12.
Figure 13:
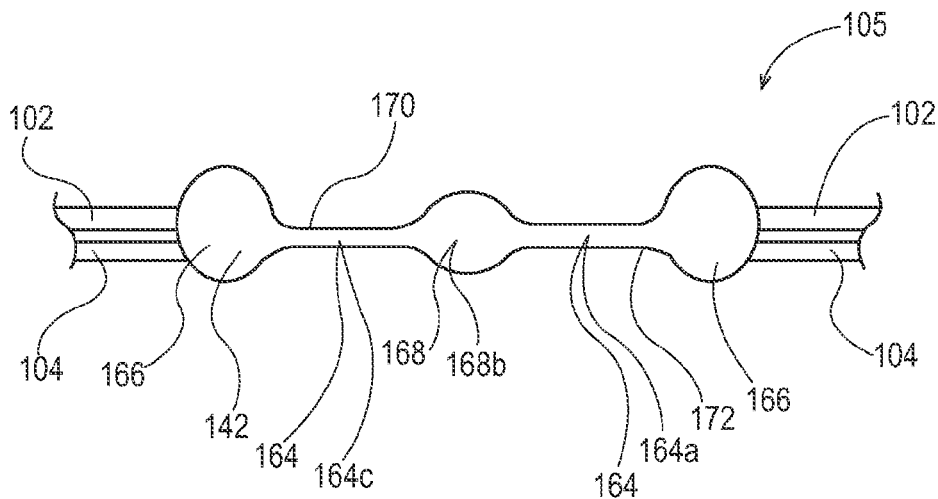
FIG. 13 is a cross-sectional view of the bond region of FIG. 11 taken along line 13-13.
Figure 14:
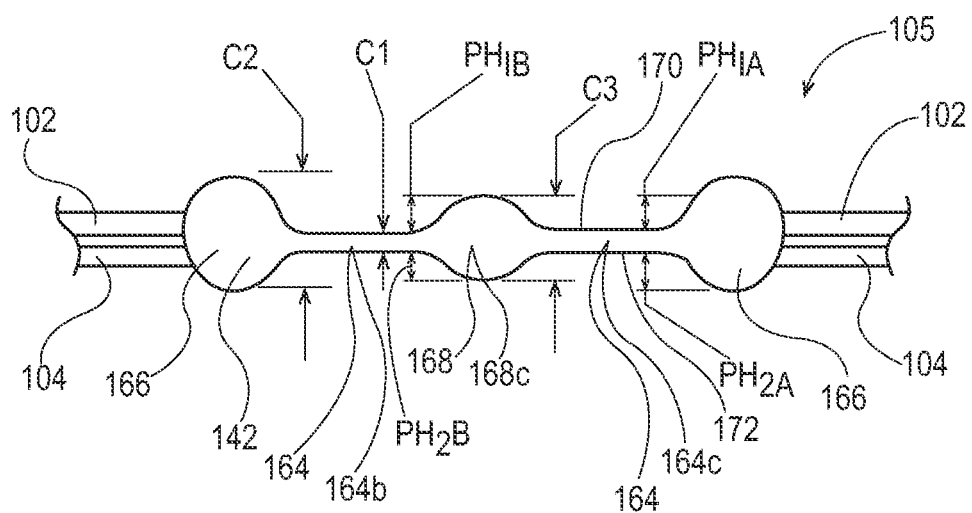
FIG. 14 is a cross-sectional view of the bond region of FIG. 11 taken along line 14-14.

It is to be appreciated that bonds 142 formed with the methods and apparatuses herein may have regions of varying thicknesses or calipers. As shown in FIGS. 12-14, the discrete bond 142 includes a first surface 170 opposite a second surface 172. A such, the bond may have: a first thickness, $C_1$; between the first surface 170 and the second surface 172 in the membrane regions 164; a second thickness, $C_2$; between the first surface 170 and the second surface 172 in the outer grommet region 166; and a third thickness, $C_3$; between the first surface 170 and the second surface 172 in the gap grommet region 168. In some embodiments, the second thickness, $C_2$, and the third thickness, $C_3$, may both be greater than the first thickness, $C_1$, and in some embodiments, the second thickness, $C_2$, may also be greater than the third thickness, $C_3$. In other embodiments, the second thickness, $C_2$, may be the same as or less than the third thickness, $C_3$. It is also to be appreciated that bonds 142 formed with the methods and apparatuses herein may have varying regions of different basis weights. For example, with continued reference to FIGS. 12-14, the membrane region 164 may have a first basis weight, $BW_1$; the outer grommet region 166 may have a second basis weight, $BW_2$; and the gap grommet region 168 may have a third basis weight, $BW_3$. In some embodiments, the second basis weight, $BW_2$, and the third basis weight, $BW_3$, may both be greater than the first basis weight, $BW_1$, and in some embodiments, the second basis weight, $BW_2$, may also be greater than the third basis weight, $BW_3$. In other embodiments, the second basis weight, $BW_2$, may be the same as or less than the third basis weight, $BW_3$.

It is also to be appreciated that bonds 142 formed with the methods and apparatuses herein may have varying regions of different opacities. For example, the membrane regions 164 may define a first opacity; the outer grommet region 166 may define a second opacity; and the gap grommet region 168 may define a third opacity. In some embodiments, the second and third opacities are greater than the first opacity.

It is to be appreciated that bonds having various different characteristics may be formed with the apparatuses and methods herein. For example, in some embodiments wherein the bond 142 is formed by compressing two substrates between the pattern surface 118 and a relatively smooth outer circumferential surface 114 of an anvil 110, the first, second, and third regions of the bond may protrude from the respective surfaces 170, 172 by different distances. For example, as shown in FIG. 14, the outer grommet region 166 defines a first maximum protrusion height, $PH_{1A}$, with respect to the first surface 170 and defines a second maximum protrusion height, $PH_{2A}$, with respect to the second surface 172. In some embodiments, the first maximum protrusion height, $PH_{1A}$, is greater than the second maximum protrusion height, $PH_{2A}$. In addition, the bond may be configured such that the gap grommet region 168 defines a first maximum protrusion height, $PH_{1B}$, with respect to the first surface 170 and defines a second maximum protrusion height, $PH_{2B}$, with respect to the second surface 172. In some embodiments, the first maximum protrusion height, $PH_{1B}$, is greater than the second maximum protrusion height, $PH_{2B}$. When using the bonding apparatuses and methods herein to make absorbent articles, such as diapers for example, the bonds may be positioned on the article such that the bond surfaces having relatively higher protrusion heights face away from the wearer of the article.

It is to be appreciated that the bonding apparatus 100 may also be configured in various different ways. For example, different types of motor arrangements may be used to rotate the pattern roll 106 and anvil roll 110. For example, the pattern roll 106 and the anvil roll 110 may be driven independently with two independent motors. In addition, the nip pressure between pattern surface and the anvil roll may be generated in various ways. For example, as previously mentioned, the pattern roll may be biased toward anvil roll; the anvil roll may be biased toward the pattern roll; or the pattern and anvil rolls may be biased toward each other. The biasing of the rolls may be accomplished in various ways, such as described for example in U.S. Pat. No. 4,854,984. In some embodiments, the bonding apparatus 100 is configured to define a nip pressure above 60,000 PSI between the pattern surface 118 and the anvil roll 110. In some embodiments, the bonding apparatus 100 is configured to define a nip pressure from about 40,000 PSI to about 60,000 PSI between the pattern surface 118 and the anvil roll 110. In some embodiments, the bonding apparatus 100 is configured to define a nip pressure of about 40,000 PSI between the pattern surface 118 and the anvil roll 110. In some embodiments, the bonding apparatus 100 is configured to define a nip pressure of about 50,000 PSI between the pattern surface 118 and the anvil roll 110. In some embodiments, the bonding apparatus 100 is configured to define a nip pressure of about 60,000 PSI between the pattern surface 118 and the anvil roll 110. It is also to be appreciated that the pattern roll and/or the anvil roll may be heated.

It is to be appreciated that the apparatuses and methods herein can be used to bond various types of substrates together. For example, in some embodiments the apparatus may used to bond nonwoven substrates, such as for example, polypropylene nonwoven, polyethylene film, bi-component nonwoven or film, polyethylene terephthalate nonwoven or film. In some embodiments, the apparatuses and methods herein may be used to bond a substrate which includes a mixture of cellulosic fibers and polyethylene or polyethylene-polypropylene bicomponent fibers or particulate. In some embodiments, the substrates may have a basis weight of about 6 gsm to about 100 gsm. Other types of substrates can be sandwiched in between two layers of nonwovens or films.

As previously mentioned, the bonding apparatuses and methods herein may used to bond various types of components used in the manufacture of different types of absorbent articles. To help provide additional context to the previous discussion of the process and apparatus embodiments, the following provides a general description of absorbent articles in the form of diapers that include components may be bonded with the methods and apparatuses disclosed herein.

Figure 15:
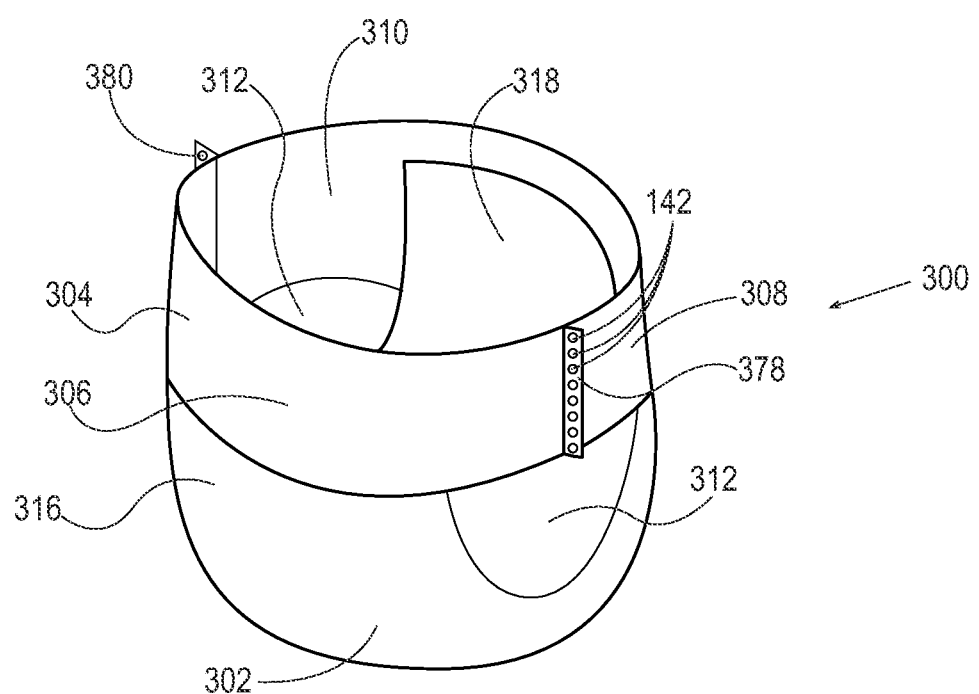
FIG. 15 is a perspective view of a diaper pant.
Figure 16:
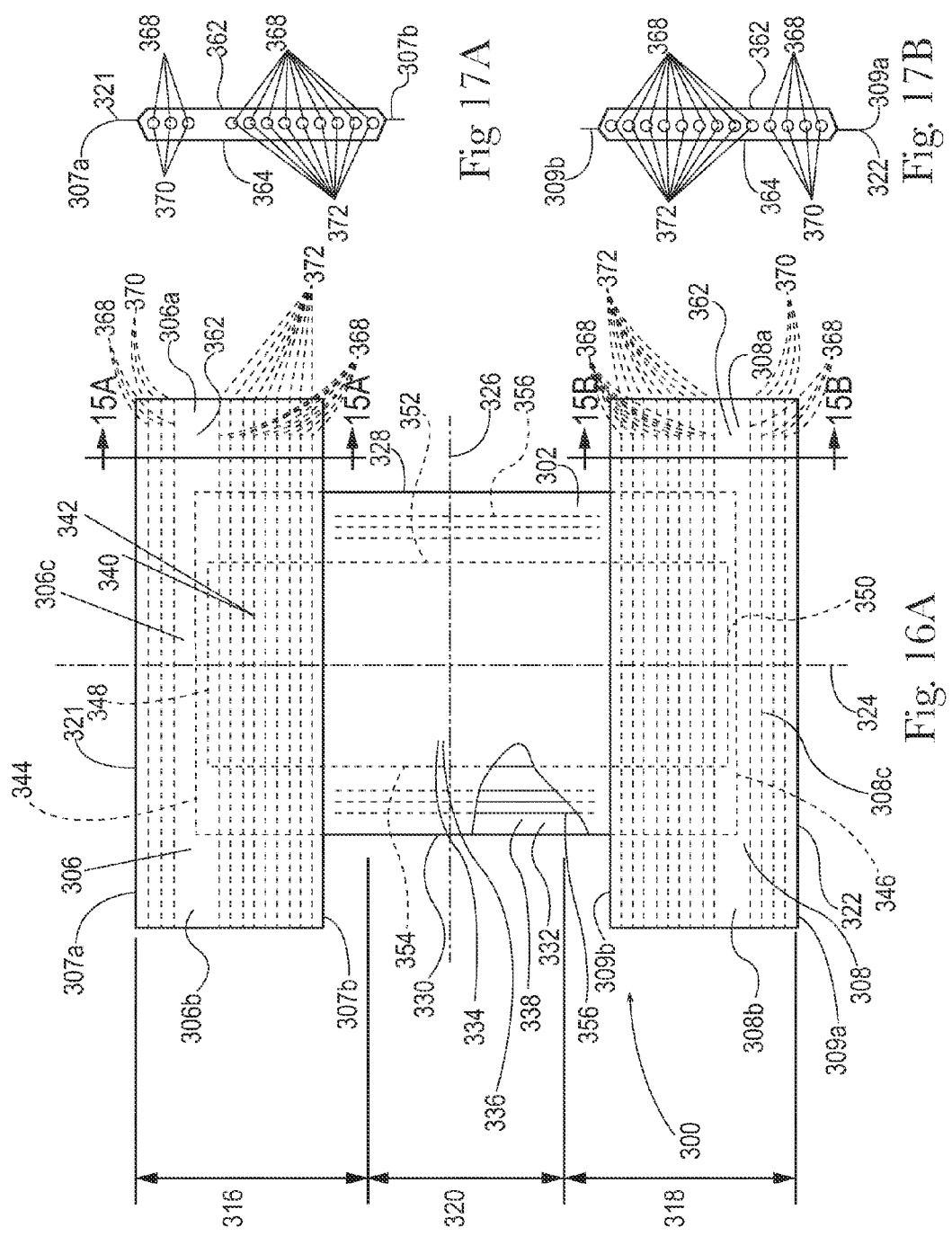
FIG. 16A is a partially cut away plan view of the diaper pant shown in FIG. 15.
FIG. 16B is a partially cut away plan view of a second embodiment of a diaper pant.

For the purposes of a specific illustration, FIGS. 15 and 16A show an example of a diaper pant 300 that may be assembled in accordance with the apparatuses and methods disclosed herein. In particular, FIG. 15 shows a perspective view of a diaper pant 300 in a pre-fastened configuration, and FIG. 16A shows a plan view of the diaper pant 300 with the portion of the diaper that faces away from a wearer oriented toward the viewer. The diaper pant 300 shown in FIGS. 15 and 16A includes a chassis 302 and a ring-like elastic belt 304. As discussed below in more detail, a first elastic belt 306 and a second elastic belt 308 are connected together to form the ring-like elastic belt 304.

With continued reference to FIG. 16A, the chassis 302 includes a first waist region 316, a second waist region 318, and a crotch region 320 disposed intermediate the first and second waist regions. The first waist region 316 may be configured as a front waist region, and the second waist region 318 may be configured as back waist region. In some embodiments, the length of each of the front waist region, back waist region, and crotch region may be ⅓ of the length of the absorbent article 300. The diaper 300 may also include a laterally extending front waist edge 321 in the front waist region 316 and a longitudinally opposing and laterally extending back waist edge 322 in the back waist region 318. To provide a frame of reference for the present discussion, the diaper 300 and chassis 302 of FIG. 16A are shown with a longitudinal axis 324 and a lateral axis 326. In some embodiments, the longitudinal axis 324 may extend through the front waist edge 321 and through the back waist edge 322. And the lateral axis 326 may extend through a first longitudinal or right side edge 328 and through a midpoint of a second longitudinal or left side edge 330 of the chassis 302.

As shown in FIGS. 15 and 16A, the diaper pant 300 may include an inner, body facing surface 332, and an outer, garment facing surface 334. The chassis 302 may include a backsheet 336 and a topsheet 338. The chassis 302 may also include an absorbent assembly 340, including an absorbent core 342, disposed between a portion of the topsheet 338 and the backsheet 336. As discussed in more detail below, the diaper 300 may also include other features, such as leg elastics and/or leg cuffs to enhance the fit around the legs of the wearer.

As shown in FIG. 16A, the periphery of the chassis 302 may be defined by the first longitudinal side edge 328, a second longitudinal side edge 330, a first laterally extending end edge 344 disposed in the first waist region 316, and a second laterally extending end edge 346 disposed in the second waist region 318. Both side edges 328 and 330 extend longitudinally between the first end edge 344 and the second end edge 346. As shown in FIG. 16A, the laterally extending end edges 344 and 346 are located longitudinally inward from the laterally extending front waist edge 321 in the front waist region 316 and the laterally extending back waist edge 322 in the back waist region 318. When the diaper pant 300 is worn on the lower torso of a wearer, the front waist edge 321 and the back waist edge 322 of the chassis 302 may encircle a portion of the waist of the wearer.

At the same time, the chassis side edges 328 and 330 may encircle at least a portion of the legs of the wearer. And the crotch region 320 may be generally positioned between the legs of the wearer with the absorbent core 342 extending from the front waist region 316 through the crotch region 320 to the back waist region 318.

It is to also be appreciated that a portion or the whole of the diaper 300 may also be made laterally extensible. The additional extensibility may help allow the diaper 300 to conform to the body of a wearer during movement by the wearer. The additional extensibility may also help, for example, the user of the diaper 300, including a chassis 302 having a particular size before extension, to extend the front waist region 316, the back waist region 318, or both waist regions of the diaper 300 and/or chassis 302 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 300 may include a backsheet 336. The backsheet 336 may also define the outer surface 334 of the chassis 302. The backsheet 336 may be impervious to fluids (e.g., menses, urine, and/or runny feces) and may be manufactured from a thin plastic film, although other flexible liquid impervious materials may also be used. The backsheet 336 may prevent the exudates absorbed and contained in the absorbent core from wetting articles which contact the diaper 300, such as bedsheets, pajamas and undergarments. The backsheet 336 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 336 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 336 may also be embossed and/or matte-finished to provide a more clothlike appearance. Further, the backsheet 336 may permit vapors to escape from the absorbent core (i.e., the backsheet is breathable) while still preventing exudates from passing through the backsheet 336. The size of the backsheet 336 may be dictated by the size of the absorbent core 342 and/or particular configuration or size of the diaper 300.

Also described above, the diaper pant 300 may include a topsheet 338. The topsheet 338 may also define all or part of the inner surface 332 of the chassis 302. The topsheet 338 may be compliant, soft feeling, and non-irritating to the wearer's skin. It may be elastically stretchable in one or two directions. Further, the topsheet 338 may be liquid pervious, permitting liquids (e.g., menses, urine, and/or runny feces) to penetrate through its thickness. A topsheet 338 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 338 includes fibers, the fibers may be spunbond, carded, wet-laid, meltblown, hydroentangled, or otherwise processed as is known in the art.

Topsheets 338 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 300 may also include an absorbent assembly 340 that is joined to the chassis 302. As shown in FIG. 16A, the absorbent assembly 340 may have a laterally extending front edge 348 in the front waist region 316 and may have a longitudinally opposing and laterally extending back edge 350 in the back waist region 318. The absorbent assembly may have a longitudinally extending right side edge 352 and may have a laterally opposing and longitudinally extending left side edge 354, both absorbent assembly side edges 352 and 354 may extend longitudinally between the front edge 348 and the back edge 350. The absorbent assembly 340 may additionally include one or more absorbent cores 342 or absorbent core layers. The absorbent core 342 may be at least partially disposed between the topsheet 338 and the backsheet 336 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 300 may also include elasticized leg cuffs 356. It is to be appreciated that the leg cuffs 356 can be and are sometimes also referred to as leg bands, side flaps, barrier cuffs, elastic cuffs or gasketing cuffs. The elasticized leg cuffs 356 may be configured in various ways to help reduce the leakage of body exudates in the leg regions. Example leg cuffs 356 may include those described in U.S. Pat. Nos. 3,860,003; 4,909,803; 4,695,278; 4,795,454; 4,704,115; 4,909,803; and U.S. Patent Publication No. 2009/0312730A1; and U.S. patent application Ser. No. 13/435,503, entitled "METHODS AND APPARATUSES FOR MAKING LEG CUFFS FOR ABSORBENT ARTICLES", filed on Mar. 30, 2012.

As mentioned above, diaper pants may be manufactured with a ring-like elastic belt 304 and provided to consumers in a configuration wherein the front waist region 316 and the back waist region 318 are connected to each other as packaged, prior to being applied to the wearer. As such, diaper pants may have a continuous perimeter waist opening 310 and continuous perimeter leg openings 312 such as shown in FIG. 15.

As previously mentioned, the ring-like elastic belt 304 is defined by a first elastic belt 306 connected with a second elastic belt 308. As shown in FIG. 16A, the first elastic belt 306 defines first and second opposing end regions 306a, 306b and a central region 306c, and the second elastic 308 belt defines first and second opposing end regions 308a, 308b and a central region 308c.

The central region 306c of the first elastic belt is connected with the first waist region 316 of the chassis 302, and the central region 308c of the second elastic belt 308 is connected with the second waist region 316 of the chassis 302. As shown in FIG. 15, the first end region 306a of the first elastic belt 306 is connected with the first end region 308a of the second elastic belt 308 at first side seam 378, and the second end region 306b of the first elastic belt 306 is connected with the second end region 308b of the second elastic belt 308 at second side seam 380 to define the ring-like elastic belt 304 as well as the waist opening 310 and leg openings 312. As discussed in more detail below, bonding apparatuses 100 herein may be used to create discrete bond regions 142 that connect first and second elastic belts 306, 308 together at the first and second side seams 378, 380.

As shown in FIGS. 16A, 17A, and 17B, the first elastic belt 306 also defines an outer lateral edge 307a and an inner lateral edge 307b, and the second elastic belt 308 defines an outer lateral edge 309a and an inner lateral edge 309b. The outer lateral edges 307a, 307b may also define the front waist edge 320 and the laterally extending back waist edge 322. The first elastic belt and the second elastic belt may also each include an outer, garment facing layer 362 and an inner, wearer facing layer 364. It is to be appreciated that the first elastic belt 306 and the second elastic belt 308 may comprise the same materials and/or may have the same structure. In some embodiments, the first elastic belt 306 and the second elastic belt may comprise different materials and/or may have different structures. It should also be appreciated that the first elastic belt 306 and the second elastic belt 308 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 306, 308 may also each include belt elastic material interposed between the outer layer 362 and the inner layer 364. The belt elastic material may include one or more elastic elements such as strands, ribbons, or panels extending along the lengths of the elastic belts. As shown in FIGS. 16A, 17A, and 17B, the belt elastic material may include a plurality of elastic strands 368 which may be referred to herein as outer, waist elastics 370 and inner, waist elastics 372. As shown in FIG. 16A, the elastic strands 368 continuously extend laterally between the first and second opposing end regions 306a, 306b of the first elastic belt 306 and between the first and second opposing end regions 308a, 308b of the second elastic belt 308. In some embodiments, some elastic strands 368 may be configured with discontinuities in areas, such as for example, where the first and second elastic belts 306, 308 overlap the absorbent assembly 340. In some embodiments, the elastic strands 368 may be disposed at a constant interval in the longitudinal direction. In other embodiments, the elastic strands 368 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 302 and elastic belts 306, 308 may be configured in different ways other than as depicted in FIG. 16A. For example, FIG. 16B shows a plan view of a diaper pant 300 having the same components as described above with reference to FIG. 16A, except the first laterally extending end edge 344 of the chassis 302 is aligned along and coincides with the outer lateral edge 307*a* of the first elastic belt 306, and the second laterally extending end edge 346 is aligned along and coincides with the outer lateral edge 309*a* of the second belt 308.

Figure 18:
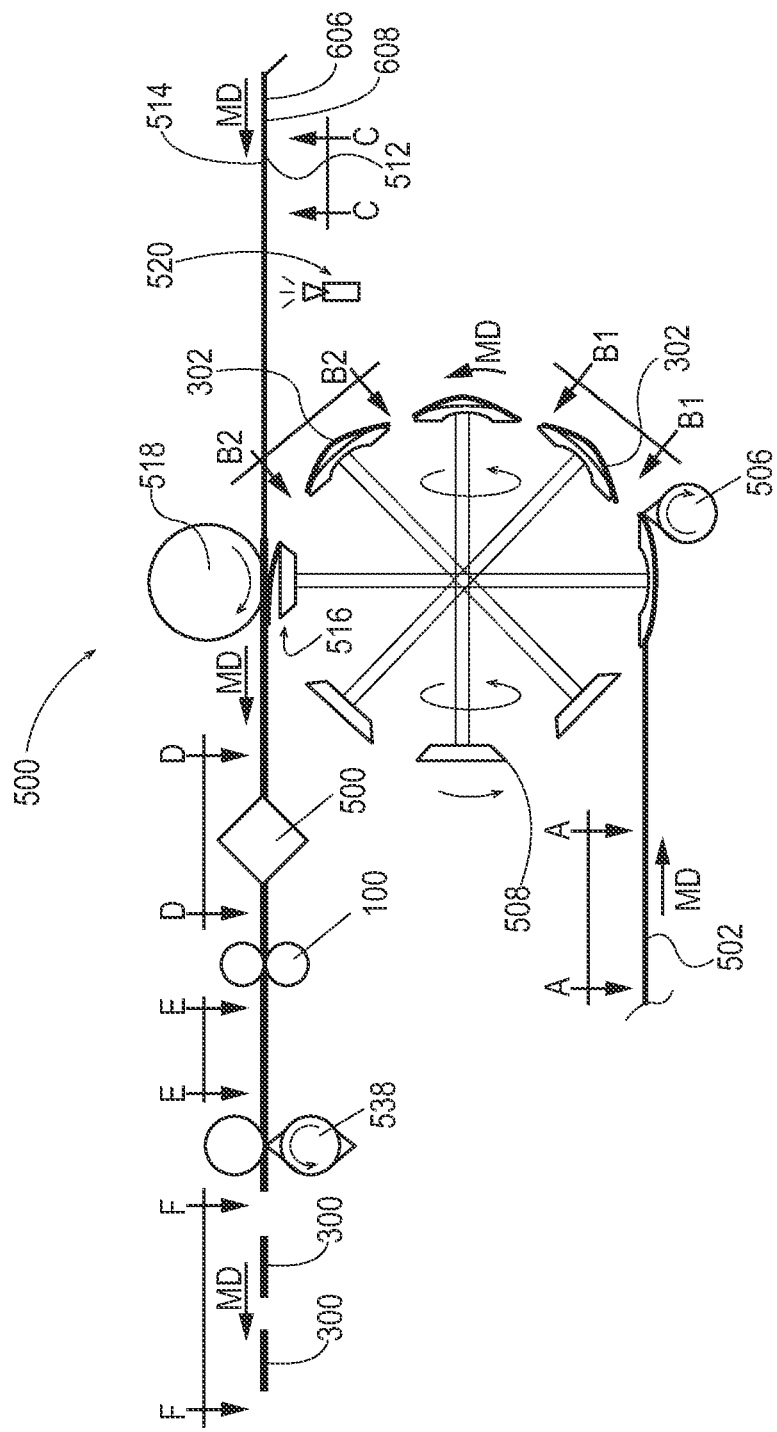
FIG. 18 is a schematic side view of a converting apparatus adapted to manufacture pre-fastened, pant diapers.

As previously mentioned, the apparatuses and methods according to the present disclosure may be utilized to assemble various components of diapers 300. For example, FIG. 18 shows a schematic view of a converting apparatus 500 adapted to manufacture pant diapers 300. The method of operation of the converting apparatus 500 may be described with reference to the various components of pant diapers 300 described above and shown in FIGS. 15 and 16A. Although the following methods are provided in the context of the diaper 300 shown in FIGS. 15 and 16A, it is to be appreciated that various embodiments of diaper pants can be manufactured according to the methods disclosed herein, such as for example, the absorbent articles disclosed in U.S. Pat. No. 7,569,039 and; U.S. Patent Publication Nos. 2005/0107764A1, US2012/0061016A1, and US2012/0061015A1, which are all hereby incorporated by reference herein.

As described in more detail below, the converting apparatus 500 shown in FIG. 18 operates to advance discrete chassis 302 along a machine direction MD such that the lateral axis of each chassis 302 is parallel with the machine direction, and wherein the chassis 302 are spaced apart from each other along the machine direction. Opposing waist regions 316, 318 of the spaced apart chassis 302 are then connected with continuous lengths of advancing first and second elastic belt substrates 606, 608. The chassis 302 are then folded along the lateral axis to bring the first and second elastic belt substrates 606, 608 into a facing relationship, and the first and second elastic belt substrates are connected together along regions 536 intermittently spaced along the machine direction, wherein each region 536 may include one or more discrete bond sites 142. And the elastic belt substrates 606, 608 are cut along the regions 536 to create discrete diapers 300, such as shown in FIG. 15.

As shown in FIGS. 18 and 17A, a continuous length of chassis assemblies 502 are advanced in a machine direction MD to a carrier apparatus 508 and cut into discrete chassis 302 with knife roll 506. The continuous length of chassis assemblies may include absorbent assemblies 340 sandwiched between topsheet material 338 and backsheet material 336, leg elastics, barrier leg cuffs and the like. A portion of the chassis assembly is cut-away to show a portion of the topsheet material 338 and an absorbent assembly 340.

After the discrete absorbent chassis 302 are cut by the knife roll 506, the carrier apparatus 508 rotates and advances the discrete chassis 302 in the machine direction MD in the orientation shown in FIG. 19B1, wherein the longitudinal axis 324 of the chassis 302 is generally parallel with the machine direction MD. While the chassis 302 shown in FIG. 19B1 is shown with the second laterally extending end edge 346 as a leading edge and the first laterally extending end edge 344 as the trailing edge, it is to be appreciated that in other embodiments, the chassis 302 may be advanced in other orientations. For example, the chassis may be oriented such that the second laterally extending end edge 346 is a trailing edge and the first laterally extending end edge 344 is a leading edge. The carrier apparatus 508 also rotates while at the same time changing the orientation of the advancing chassis 302. The carrier apparatus 508 may also change the speed at which the chassis 302 advances in the machine direction MD. It is to be appreciated that various forms of carrier apparatuses may be used with the methods herein, such as for example, the carrier apparatuses disclosed in U.S. Pat. No. 7,587,966. FIG. 19B2 shows the orientation of the chassis 302 on the carrier apparatus 508 while advancing in the machine direction. More particularly, FIG. 19B2 shows the chassis 302 with the lateral axis 326 of the chassis 302 generally parallel with the machine direction MD, and wherein the second longitudinal side edge 330 is the leading edge and the first longitudinal side edge 328 is the trailing edge.

As discussed below with reference to FIGS. 18, 19C, 19D, 19E, and 19F, the chassis 302 are transferred from the carrier apparatus 508 and combined with advancing, continuous lengths of belt substrates 606, 608, which are subsequently cut to form first and second elastic belts 306, 308 on diapers 300.

Figure 17:
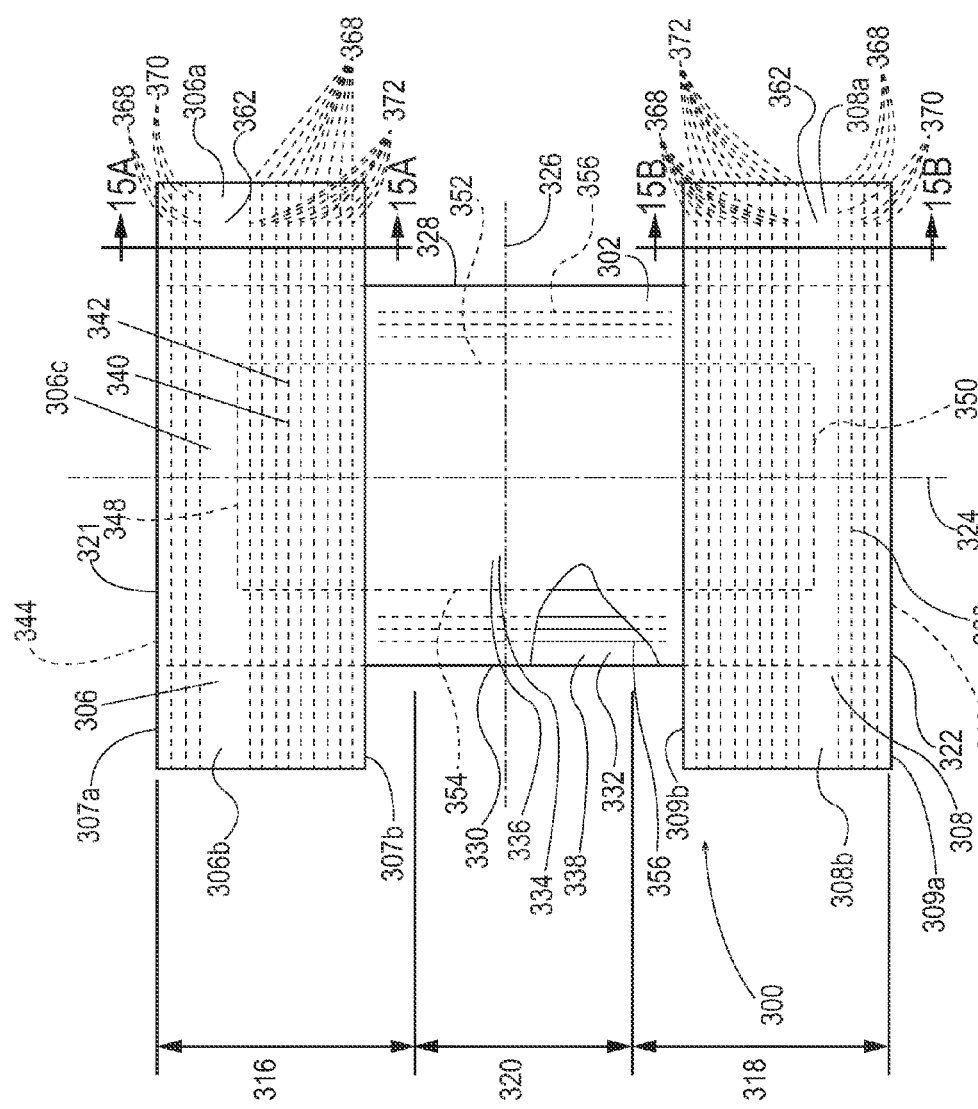
FIG. 17A is a cross-sectional view of the diaper pants of FIGS. 16A and 16B taken along line 17A-17A.
FIG. 17B is a cross-sectional view of the diaper pants of FIGS. 16A and 16B taken along line 17B-17B.

With reference to FIGS. 17 and 19C, the chassis 302 are transferred from the carrier apparatus 508 to a nip 516 between the carrier apparatus 508 and a carrier apparatus 518 where the chassis 302 is combined with continuous lengths of advancing front belt 606 and back belt 608 substrate material. The front belt substrate material 606 and the back belt substrate material 608 each define a wearer facing surface 512 and an opposing garment facing surface 514. The wearer facing surface 512 of the first belt substrate 606 may be combined with the garment facing surface 334 of the chassis 302 along the first waist region 316, and the wearer facing surface 512 of the second belt substrate 608 may be combined with the garment facing surface 334 of the chassis 302 along the second waist region 318. As shown in FIG. 18, adhesive 520 may be intermittently applied to the wearer facing surface 512 of the first and second belt substrates 606, 608 before combining with the discrete chassis 302 at the nip 516 between roll 518 and the carrier apparatus 508.

With reference to FIGS. 18 and 19D, a continuous length of absorbent articles 600 are defined by multiple discrete chassis 302 spaced from each other along the machine direction MD and connected with each other by the second belt substrate 608 and the first belt substrate 606. As shown in FIG. 18, the continuous length of absorbent articles 600 advances from the nip 516 to a folding apparatus 500. At the folding apparatus 500, each chassis 302 is folded in the cross direction CD along a lateral axis 326 to place the first waist region 316, and specifically, the inner, body facing surface 332 into a facing, surface to surface orientation with the inner, body surface 332 of the second waist region 318. The folding of the chassis also positions the wearer facing surface 512 of the second belt substrate 608 extending between each chassis 302 in a facing relationship with the wearer facing surface 512 of the first belt substrate 606 extending between each chassis 302. As shown in FIGS. 18, 19D, and 19E, the folded discrete chassis 302 connected with the first and second belt substrates 606, 608 are advanced from the folding apparatus 500 to a bonder apparatus 100, such as described above. The bonder apparatus 100 operates to bond an overlap area 362, thus creating discrete bond sites 142. The overlap area 362 includes a portion of the second belt substrate 608 extending between each chassis 302 and a portion of the first belt substrate 606 extending between each chassis 302. As shown in FIGS. 18 and 19F, a continuous length of absorbent articles are advanced from the bonder 100 to a knife roll 538 where the regions 536 are cut into along the cross direction to create a first side seam 378 on an absorbent article 300 and a second side seam 380 on a subsequently advancing absorbent article.

Although the absorbent article is described as having a first and second belt substrate, it is to be appreciated that the absorbent article may have only one belt substrate. Further, it is to be appreciated that the chassis and belt substrate of the absorbent article may be one continuous substrate such that the overlap area is formed from the same substrate. As such, the bonder apparatus may operate to bond a continuous substrate at an overlap area to form one or more discrete bond sites.

Although the apparatuses and methods have been described in the context of the diapers 300 shown in FIGS. 15, 16A, and 16B, it is to be appreciated that the methods and apparatuses herein may be used to assemble and bond various substrates and/or elastic laminates that can be used with various process configurations and/or absorbent articles, such as for example, disclosed in U.S. Pat. No. 7,569,039; U.S. Patent Publication Nos. US2005/0107764A1, US2012/0061016A1, and US2012/0061015A1; U.S. patent application Ser. No. 13/434,984, filed on Mar. 30, 2012; U.S. patent application Ser. No. 13/435,036, filed on Mar. 30, 2012; U.S. patent application Ser. No. 13/435,063, filed on Mar. 30, 2012; U.S. patent application Ser. No. 13/435,247, filed on Mar. 30, 2012; and U.S. patent application Ser. No. 13/435,503, filed on Mar. 30, 2012, all of which are incorporated by reference herein. For example, the bonding apparatuses and methods herein can be used to apply tack-down bonds on leg cuffs, such as described in U.S. patent application Ser. No. 13/435,503, entitled "METHODS AND APPARATUSES FOR MAKING LEG CUFFS FOR ABSORBENT ARTICLES", filed on Mar. 30, 2012.

In the context of the previous discussion, the apparatuses 100 and methods herein may be used to provide for the application of bonds 142 in patterns to substrates and components during the manufacture of an absorbent article. For example, bonds 142 may be applied in various patterns to portions of any of the topsheet, backsheet, absorbent core, leg cuffs, waist feature, ears, and fastening elements during the manufacture of an absorbent article. In some instances, the adhesive may be used in combination with the bonding methods herein.

Peel Strength Test Method

Bond Strength is measured using a 180° T-peel test on a constant rate of extension tensile tester with computer interface (a suitable instrument is the MTS Model Q-Test/1 using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with smooth stainless steel faced grips, 25.4 mm in height and wider than the width of the test specimen. Air pressure supplied to the jaws is sufficient to prevent sample slippage. All testing is performed in a conditioned room maintained at about 23° C.±2 C.° and about 50° C.±2 C.° relative humidity.

Condition the samples at 23±2° C. and 50%±2% relative humidity for at least 24 hours prior to testing. Identify the bond site to be tested. The test specimen consists of the bond and the two material layers which are bonded together. Using a razor knife or scissors cut the specimen 25.4 mm±0.1 mm in the dimension parallel to the bond, and preferably 50.8 mm in the dimension perpendicular to and centered on the bond. If a 50.8 mm perpendicular length cannot be harvested from the article, attach leads made from adhesive tape (e.g., duct tape) to the specimen for use to secure it in the tensile tester's grip faces.

Program the tensile tester to perform an extension test, collecting force and extension data at an acquisition rate of 50 Hz as the crosshead raises at a rate of 304 mm/min until the two layers are separated.

Figure 22:
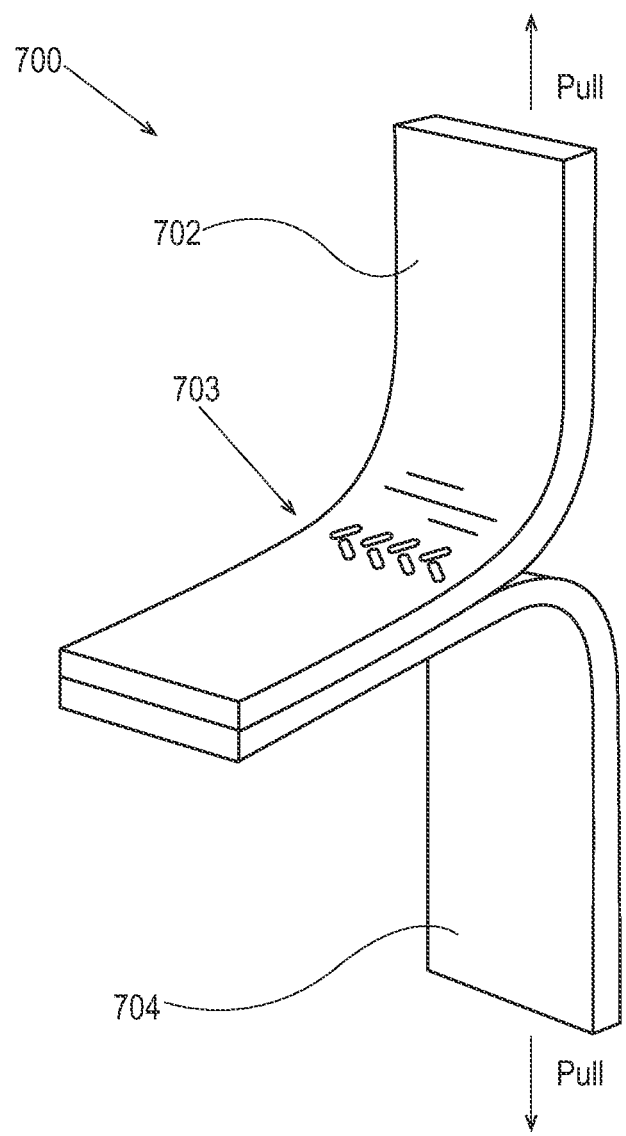
FIG. 22 illustrates an example test sample for use with the peel strength test method.

Set the gage length to 25.4 mm±0.1 mm and zero the crosshead position. Referring to FIG. 22, position the end of the first layer (or attached leader) 702 within the upper grip faces. Align the specimen 700 vertically with the bond site 703 centered between the upper and lower grip faces and close the upper grip faces. With the specimen hanging downward and not touching the bottom fixture, zero the load cell. Position the second layer (or attached leader) 704 within the lower grip faces and close. The specimen should be under enough tension to eliminate any slack, but less than 0.05 N of force on the load cell.

Start the test and collect data. From the resulting Force (N) versus Extension (mm) curve, calculate the Maximum Peak Force (N). Calculate the Bond Strength (N/m) as the Peak Force (N) divided by the specimen width (m) and record to the nearest 0.1 N/m.

Repeat the test on a total of ten substantially identical articles selecting the corresponding test site on each article. Report the average Bond Strength (N/m) to the nearest 0.1 N/m.

End of Peel Strength Test Method

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for dynamically bonding substrates, the apparatus comprising:

an anvil roll;

a means for pressing a first substrate and a second substrate against the anvil roll to form a discrete bond region between the first and second substrates such that material of the first and second substrates is yielded, the means for pressing comprising:

base circumferential surface;

a first pattern element including a first pattern surface having a first pattern area, A1, wherein A1 is greater than about 0.25 mm$^2$ and less than about 2.00 mm$^2$, wherein the first pattern element protrudes outward from the base circumferential surface to define a distance, Hp1, between the first pattern surface and the base circumferential surface, and wherein the first pattern element is bounded by a first perimeter;

a second pattern element including a second pattern surface having a second pattern area, A2, wherein A2 is greater than about 0.25 mm$^2$ and less than about 2.00 mm$^2$, wherein the second pattern element protrudes outward from the base circumferential surface to define a distance, Hp2, between the second pattern surface and the base circumferential surface, and wherein the second pattern element is bounded by a second perimeter; and a third pattern element including a third pattern surface having a third pattern area, A3, wherein A3 is greater than about 0.25 mm$^2$ and less than about 2.00 mm$^2$, wherein the third pattern element protrudes outward from the base circumferential surface to define a distance, Hp3, between the third pattern surface and the base circumferential surface, and wherein the third pattern element is bounded by a third perimeter;

wherein the first and second pattern surfaces are separated by a first gap having a minimum width, D1, wherein the first and third pattern surfaces are separated by a second gap having a minimum width, D2, and wherein the second and third pattern surfaces are separated by a third gap having a minimum width, D3, and wherein D1, D2, and D3 are greater than 0.20 mm and less than about 3.00 mm; and wherein the means for pressing is adjacent the anvil roll to define a nip between the first, second, and third pattern surfaces and the anvil roll; and wherein some yielded material between the pattern surface and the anvil roll is fused together, wherein some yielded material flows out from between the first pattern surface and the anvil roll to the first gap, and wherein some yielded material flows out from between the second pattern surface and the anvil to the first gap and the third gap; and wherein the means for pressing is biased toward the anvil roll to define a nip pressure of greater than about 40,000 PSI and less than about 60,000 PSI between each pattern surface and the anvil roll.

2. The apparatus of claim 1, wherein at least one of A1, A2, and A3 is about 0.70 mm$^2$.

3. The apparatus of claim 2, wherein at least one of D1, D2, and D3 is about 0.30 mm.

4. The apparatus of claim 3, wherein the nip pressure is about 40,000 PSI.

5. The apparatus of claim 1, wherein A1, A2, and A3 are substantially the same.

6. The apparatus of claim 5, wherein D1, D2, and D3 are substantially the same.

7. The apparatus of claim 1, wherein each of the first perimeter, second perimeter, and third perimeter defines an elliptical shape.

* * * * *